(12) United States Patent
Ranalletta et al.

(10) Patent No.: US 7,922,711 B2
(45) Date of Patent: Apr. 12, 2011

(54) STERILE DOCKING APPARATUS AND METHOD

(75) Inventors: Joseph Vincent Ranalletta, Englewood, CO (US); Robert S. Brereton, Centennial, CO (US); Kristine Michelle Cohrs, Englewood, CO (US)

(73) Assignee: Baxa Corporation, Englewood, CO (US)

( * ) Notice: Subject to any disclaimer, the term of this patent is extended or adjusted under 35 U.S.C. 154(b) by 1336 days.

(21) Appl. No.: 11/433,143

(22) Filed: May 10, 2006

(65) Prior Publication Data

US 2006/0271000 A1 Nov. 30, 2006

Related U.S. Application Data

(63) Continuation-in-part of application No. 11/125,774, filed on May 10, 2005, now Pat. No. 7,611,505.

(51) Int. Cl.
*A61M 39/18* (2006.01)
(52) U.S. Cl. ........................................................ 604/539
(58) Field of Classification Search .................. 604/256, 604/246, 538, 539, 533, 905; 251/149, 149.1–149.5, 251/149.7–149.9
See application file for complete search history.

(56) References Cited

U.S. PATENT DOCUMENTS

| | | | |
|---|---|---|---|
| 4,411,656 A | 10/1983 | Cornett, III | 604/212 |
| 4,425,113 A | 1/1984 | Bilstad | 604/6 |
| 4,534,573 A | 8/1985 | Somers | 279/149 |
| 4,597,758 A | 7/1986 | Aalto et al. | 604/156 |
| 4,821,996 A | 4/1989 | Bellotti et al. | 251/9 |
| 5,265,822 A | 11/1993 | Shober, Jr. et al. | 242/388.2 |
| 5,295,957 A | 3/1994 | Aida et al. | 604/74 |
| 5,524,783 A | 6/1996 | Popoff | 215/386 |
| 5,535,785 A | 7/1996 | Werge et al. | 137/843 |
| 5,620,427 A | 4/1997 | Werschmidt et al. | 604/283 |
| 5,676,346 A | 10/1997 | Leinsing | 251/149.1 |
| 5,681,279 A | 10/1997 | Roper et al. | 604/57 |
| 5,699,821 A | 12/1997 | Paradis | 137/1 |
| 5,702,374 A | 12/1997 | Johnson | 604/283 |
| 5,730,723 A | 3/1998 | Castellano et al. | 604/68 |
| 5,775,671 A | 7/1998 | Cote, Sr. | 251/149.8 |
| 5,782,816 A | 7/1998 | Werschmidt et al. | 604/256 |
| 5,788,215 A | 8/1998 | Ryan | 251/149.6 |
| 5,807,345 A | 9/1998 | Grabenkort | 604/199 |
| 5,820,602 A | 10/1998 | Kovelman et al. | 604/187 |
| 5,851,201 A | 12/1998 | Ritger et al. | 604/240 |
| 5,855,230 A | 1/1999 | Guala et al. | 138/89 |
| 5,947,954 A | 9/1999 | Bonaldo | 604/533 |
| 5,954,313 A | 9/1999 | Ryan | 251/149.1 |
| 5,984,373 A | 11/1999 | Fitoussi et al. | 285/92 |
| 6,032,926 A | 3/2000 | Fuchs | 251/149.4 |

(Continued)

*Primary Examiner* — Kevin C Sirmons
*Assistant Examiner* — Michael J Anderson
(74) *Attorney, Agent, or Firm* — Marsh Fischmann & Breyfogle LLP

(57) ABSTRACT

An improved sterile docking apparatus for a medical-liquid, male connectors includes a holding member having an opening for matably receiving a nozzle end of a medical-liquid, male connector therethrough, and a deformable member disposed across the opening, wherein the deformable member is deformable to envelop and thereby isolate a nozzle end of a medical-liquid, male connector that is inserted into the opening of the holding member. The deformable member may be resilient, wherein it substantially returns to an initial configuration after removal of a nozzle end of a medical-liquid, male connector from the opening of the holding member. An interconnection surface may be provided on the holding member of the docking apparatus to interface with a complimentary interconnection surface of a medical-liquid, male connector so as to maintain the nozzle end of the medical-liquid, male connector in an enveloped position during docking.

46 Claims, 21 Drawing Sheets

U.S. PATENT DOCUMENTS

| | | | |
|---|---|---|---|
| 6,039,302 A * | 3/2000 | Cote et al. | 251/149.1 |
| 6,063,062 A | 5/2000 | Paradis | 604/249 |
| 6,152,913 A | 11/2000 | Feith et al. | 604/533 |
| 6,158,458 A | 12/2000 | Ryan | 137/515.5 |
| 6,171,287 B1 * | 1/2001 | Lynn et al. | 604/256 |
| 6,217,560 B1 | 4/2001 | Ritger et al. | 604/243 |
| RE37,357 E | 9/2001 | Lynn | 604/533 |
| 6,332,633 B1 | 12/2001 | Fitoussi et al. | 285/332 |
| 6,394,983 B1 | 5/2002 | Mayoral et al. | 604/192 |
| 6,732,872 B1 | 5/2004 | Gregro et al. | 215/11.3 |

* cited by examiner

STERILE DOCKING APPARATUS AND METHOD

CROSS-REFERENCE TO RELATED APPLICATIONS

This application claims priority as a continuation-in-part application to U.S. patent application Ser. No. 11/125,774 filed on May 10, 2005 now U.S. Pat. No. 7,611,505, entitled "STERILE DOCKING APPARATUS AND METHOD", the entirety of which is hereby incorporated by reference.

FIELD OF THE INVENTION

The present invention relates to the field of medical liquid administration, and more particularly, to an improved docking apparatus and method for enhancing the maintenance of sterility of a nozzle end of a male connector fluidly interconnected or interconnectable to a medical liquid source during one or repeated periods of non-use (e.g. between successive administrations of a medical liquid through a vascular catheter over an extended time period).

BACKGROUND OF THE INVENTION

Numerous techniques are employed for the administration of "medical liquids" (e.g. liquid medication and flush solutions) to a patient. In particular, where repeated medication infusions are required, medical liquids are often administered via the use of a vascular access catheter that is fluidly interconnected or interconnectable to one or more medical liquid sources via an associated tubing line set. Typically, the catheter is inserted into the vein of a patient and left there for multiple intravenous (IV) infusions during an extended course of medication therapy. By way of example, the time period between IV drug infusions may be between about 4 to 24 hours, wherein the IV liquid medication source is typically replaced after each dose infusion.

In conjunction with extended therapy applications, a desirable practice is to disconnect a vascular catheter from a medical liquid source(s) between infusions. In this regard, most patients receiving IV medication therapy are ambulatory to some degree and benefit from not being continuously connected to a medical liquid source(s).

To facilitate the ready and repeated connection/disconnection of a vascular catheter and medical liquid source(s), while avoiding the use of needle-type arrangements (e.g. arrangements where sharp/blunt needle ends are inserted into specialized vascular catheter connection ports having a piercable/slit stopper), complimentary female and male connectors are often utilized (e.g. male and female luer connectors). For purposes hereof, a "male connector" generally refers to any fluid connector having a nozzle end that projects into a "female connector" upon interconnection therewith, wherein fluid transfer between the male and female connector may be realized. In this regard, for example, a female connector may be fluidly interconnected as an access port to the vascular catheter and a complimentary male connector may be fluidly interconnected or readily interconnectable to a medical liquid source(s).

In order to maintain sterility, the medical-liquid, male connector is typically covered with a new cap after each disconnection from the female connector, and a depressible member of the medical-liquid, female connector is contacted with an antibacterial material (e.g. an alcohol solution) before each interconnection with the male connector. Such an approach entails the unpackaging, use and disposal of multiple caps over an extended medication therapy. For example, where liquid medication is administered at least every four hours over a three-day period at least 18 caps would be required to maintain the sterility of the medical-liquid, male connector. As may be appreciated, cap-related costs, medical personnel time expenditures and inventory management implications associated with this approach can become quite significant.

SUMMARY OF THE INVENTION

In view of the foregoing, a broad objective of the present invention is to facilitate both the sterile and cost-effective handling of medical-liquid, male connectors that are interconnected/disconnected from complimentary female connectors more than once in the course of medical-liquid delivery, and particularly in applications where multiple vascular catheter connections/disconnections with a medical liquid source(s) are entailed in the course of IV medication therapy.

Further, a related objective of the present invention is to address the broad objective in a manner that reduces medical accessory costs, inventory management requirements and medical personnel time expenditures.

Another objective of the present invention is to provide for enhanced sterile handling of medical-liquid, male connectors during periods of non-use in a manner that is both convenient and space-efficient at a patient care site.

One or more of the above objectives and additional advantages are realized by the inventive docking apparatus and method disclosed herein. In particular, a dedicated apparatus is provided for docking a medical-liquid, male connector that is fluidly interconnected or connectable to a medical liquid source during one or repeated periods of non-use. The docking apparatus comprises a holding member having an opening for matably receiving a nozzle end of a medical-liquid, male connector therethrough, and a deformable member disposed across the opening. Of note, the deformable member is deformable so as to isolate a nozzle end of a medical-liquid, male connector that engages the deformable member upon insertion through the opening of the holding member. That is, the deformable member is provided to deform through the opening of the holding member upon engagement by the nozzle end of a medical-liquid, male connector and thereby envelop the nozzle end in a tent-like manner through the opening so as to maintain the sterility of the nozzle end during docking use of the inventive apparatus.

In one characterization, the holding member may include a tubular portion that defines the opening, wherein an isolating portion of the deformable member is deformable for positioning over the nozzle end of a medical-liquid, male connector inserted through the opening and between a portion of the tubular portion and a distal sidewall portion of the nozzle end of the medical-liquid, male connector. In another characterization, at least an isolating portion of the deformable member is deformable from an initial configuration (e.g. a sheet-like configuration) into a cup-shaped, or u-shaped, configuration by and for isolation of the nozzle end of a medical-liquid, male connector inserted through the opening of the holding member. Of additional note, the deformable member is preferably provided so that an isolating portion thereof reconfigures from a deformed configuration (e.g. a cup-shaped configuration) back to an initial configuration upon removal of the nozzle end of a medical-liquid, male connector from the opening, thereby facilitating reuse of the docking apparatus.

In certain arrangements, the deformable member may comprise an antimicrobial material. For example, the deformable member may comprise metal ions that provide an antibacterial effect (e.g. silver salts such as sulfadiazine).

In one aspect of the invention, the deformable member may be disposed to extend across an opening at one end of the holding member, thereby facilitating ready access to the deformable member for cleaning and contact with an antibacterial material prior to docking use. In one arrangement, the deformable member may be disposed over an opening at the top end of a tubular portion of the holding member. In another arrangement, the deformable member may be fixedly interconnected about the periphery of an opening of a ring-shaped portion of a holding member. In yet another arrangement, the deformable member may be disposed to extend across an opening of a tubular portion of the holding member in recessed relation to a top end of the tubular portion.

In another aspect of the invention, the deformable member may be provided to define a continuous outer surface portion across the opening at one end of the holding member prior to insertion of a nozzle end of a medical-liquid, male connector. The continuous surface portion is preferably substantially planar or convex, and less preferably, concave. As may be appreciated, the provision of a continuous outer surface portion (e.g. having no creases, pockets or the like) on the deformable member further facilitates cleaning and the application of an antibacterial material thereto prior to engagement with the nozzle end of a medical-liquid, male connector. Additionally, such outer surface portion facilitates contact engagement across an entire distal edge of a nozzle end of a medical-liquid, male connector during docking use. Further, the provision of a continuous outer surface portion on the deformable member facilitates substantial avoidance of any fluid retention thereupon after removal of a medical-liquid, male connector from the docking apparatus.

In yet another aspect, the deformable member may be provided to extend over, and laterally and outwardly away from, an opening at one end of the holding member. Preferably, the deformable member extends over and laterally beyond the entire periphery of an opening at one end of a tubular portion of the holding member.

At least a portion of the deformable member may be of a resilient nature, wherein a surface portion of the deformable member that engages a nozzle end of a medical-liquid, male connector (e.g. entirely across and about the periphery thereof) may apply a predetermined minimum force (e.g. at least about 1 psi and preferably between about 1 psi and 6 psi) across the lateral extent of the nozzle end. In turn, a pressure and hermetic seal may be advantageously realized. In this regard, the ability to realize such a seal facilitates docking of a male connector in fluid communication with a medical-liquid source (e.g. a bag of saline solution supported in a position to create a head pressure of about 3-4 feet).

In one arrangement, an outer surface portion of the deformable member may include a small, raised pimple centered relative to the opening to facilitate docking. Such raised pimple may be sized for receipt within a nozzle end of a medical-liquid, male connector, thereby further enhancing male connector placement and seal realization.

In one approach, the deformable member may be defined by a T-shaped member having a cap portion that extends over and away from the holding member opening, and an adjoining leg portion that extends through the holding member opening into a tubular portion thereof. As will be further described, the leg portion may be of a resilient, or spring-like, nature so as to be depressible within a tubular portion of a holding member during docking use, and automatically spring-back and thereby reposition the cap portion in overlapping relation to the opening of the holding member after docking use.

In one embodiment, a resilient T-shaped member may include a cap portion of a plate-like, or sheet-like configuration, and an adjoining leg portion of a tubular configuration, wherein the cap portion includes a pliable, resilient, peripheral flap region that extends over and away from one end of the tubular leg portion. The tubular leg portion may comprise a plurality of undulations, thereby allowing the leg portion to be depressed from a first configuration to a second configuration in an accordion-like manner within a tubular portion of the holding member during docking use, and automatically return to the first configuration after docking use. As may be appreciated, during docking use the flap region of the plate-like cap portion may be drawn into the tubular portion of the holding member, wherein the cap portion assumes a cup-like configuration so as to envelop the nozzle end of a docked male connector. After docking, the cap portion is urged back out of the tubular portion of the holding member by the leg portion to assume its initial plate-like configuration.

As may be appreciated, numerous additional embodiments of the T-shaped member may be employed. By way of example only, the leg portion may be defined by a depressible, resilient foam member, a metal spring, and a diaphragm-like assembly (e.g. having a rigid member connected to a cap portion at one end and a spring member connected to another end).

In one approach, a T-shaped member may be provided so that the leg portion is restricted from removal through the opening. In one arrangement, the T-shaped member may comprise a leg portion that includes at least two sub-portions that are configured relative to at least two corresponding sections of a tubular portion of the holding member so that one of the leg sub-portions is restricted from passage into at least one of the sections of the tubular portion (e.g. the section nearest the opening). By way of example, a tubular leg portion may be provided with two sub-portions having differing cross-dimensions. For example, a leg portion having a plurality of undulations may comprise a first sub-portion (e.g. positionable nearest the opening) with undulations of a first maximum cross-dimension (e.g. diameter) and a second sub-portion with undulations of a greater, second maximum cross-dimension (e.g. diameter). In turn, a tubular portion of the holding member may comprise at least two sections, wherein a first section (e.g. located nearest the opening) has an inside minimum cross-dimension (e.g. diameter) that is greater than the maximum cross-dimension of the first sub-portion of the leg portion and less than the maximum cross-dimension of the second sub-portion of the leg portion, and a second section having an inside minimum cross-dimension that is greater than the maximum cross-dimension of the second sub-portion of the leg portion. As may be appreciated, such an arrangement facilitates retention of the second sub-portion of the leg portion of the T-shaped member within the second section of the tubular portion of a holding member (e.g. since the second sub-portion of the leg portion cannot non-forcibly pass through the first tubular section).

In another approach, the deformable member may be defined by a stretchable, sheet-like film member that is interconnected to the docking apparatus about a ring, wherein an operative area is defined within the ring that is greater than the area of the holding member opening. In certain arrangements, the film member may stretch across such operative area during docking use. That is, in such arrangements the film member may advantageously stretch across an area larger than the holding member opening during a first stage of docking (e.g.

until the film member is restrainably engaged between at least a portion of the interconnection surfaces of the docking apparatus and a medical-liquid, male connector), wherein further stretching during a second stage of docking is substantially limited to a smaller area of the film member. To facilitate stretching of the film member across a surface area larger than the opening of the holding member, an interconnection surface may be provided on the holding member that yields a predetermined clearance relative to a complimentary interconnection surface of a medical-liquid, male connector. For example, in arrangements where a threaded interconnection surface is provided on the outside of a tubular portion of the holding member, it may be preferable to provide a clearance between such interconnection surface and a complimentary internally threaded surface of a collar of a medical-liquid, male connector of at least 2 times and most preferably between about 2 to 4 times the thickness of the film member. Further, in such arrangements it may be preferable to provide a holding member opening whose periphery provides a predetermined clearance relative to a docked nozzle end of a medical-liquid, male connector of at least 2 times the material thickness of the film member.

In another embodiment, a film member may extend across and angle downwardly and away from a top end of a tubular portion of the holding member to define a continuous, outer surface that includes a continuous, substantially planar or convex, and less preferably, concave, outer surface portion and a surrounding (e.g. ring-shaped), conical, outer surface portion. When an interconnection surface is provided on an outside surface of a tubular portion of the holding member, the conical, outer surface portion of the film member may be provided to extend over and about the interconnection surface, wherein the film member is interposed in contact engagement with and between the interconnection surface of the holding member and a complimentary interconnection surface on the inside of a collar of a medical-liquid, male connector during docking use of the docking apparatus. As may be appreciated, such an arrangement facilitates the application of an antibacterial material to the outer surface of the film member and contact engagement thereof with an interconnection surface of a medical-liquid, male connector (e.g. internal threads of a collar) during docking use.

In arrangements where a film member is used, it is preferable for the film member to be capable of at least about 400% elongation, and more preferably at least about 700% elongation (e.g. elongation per unit length while maintaining at least a degree of elasticity sufficient to maintain contact between the film member and nozzle end of a male connector during docking use). Even more preferably, the film member may be elastic so that it is able to elastically deform during docking use and substantially return to its initial configuration after removal of a nozzle end of a medical-liquid, male connector from the holding member opening, thereby enhancing repeated docking use of the docking apparatus. More particularly, it is preferable that the film member be provided to have a modulus of elasticity of at least about 1000 psi, and even more preferably of at least about 3000 psi. By way of example, an elastic film member may comprise a polymer-based material, such as a material selected from a group comprising: thermoset rubbers and thermoplastic polyurethanes.

In another aspect of the present invention, an interconnection surface may be provided on the holding member (e.g. on an outside or inside surface of a tubular portion of the holding member), wherein the interconnection surface is adapted for selective interconnection/disconnection with a complimentary interconnection surface provided on a medical-liquid, male connector. As may be appreciated, in some arrangements the complimentary interconnection surface may be the same means that is utilized for fluidly interconnecting the medical-liquid, male connector to a patient (e.g. via a vascular catheter interface for medical-liquid administration).

In one approach, the interconnection surface may comprise a threaded surface provided on an outside surface or on an inside surface of a tubular portion of the holding member that is sized/shaped to threadably interface with a complimentary threaded surface provided on an inside surface of a collar or on an outside surface of a nozzle end, respectively, of a medical-liquid, male connector. For example, an outside surface of a tubular portion of the holding member may be threaded to interface with an internally threaded, rotatable collar of a medical-liquid, male luer connector that is utilized for selective interconnection/disconnection from a female connector fluidly interconnected with a vascular catheter.

In one embodiment, an outside surface of a tubular portion of the holding member may be provided with at least one and preferably two raised threads, that arcuately extend about the tubular portion for threadable engagement with an internally threaded collar of a medical-liquid, male connector. For example, dual threads may be provided on the tubular portion so that the leading end of each thread is offset about 150° to 210° (e.g. 180°) from the other. In one approach, each thread may be provided to spiral about 90° to 360° (e.g. 340°) around the tubular portion. Optionally, a raised rib may be provided on at least a portion of each raised thread to further facilitate a tight, interconnection with a collar of a medical-liquid, male connector. For example, in one embodiment two offset threads may be provided, wherein each thread includes an arcuate first portion that extends away from a distal end of a tubular portion (e.g. extends about 45° to 180°) and an adjoining, arcuate second portion that ends away from the first portion (e.g. extends about 45° to 180°) and includes a raised rib thereupon. As may be appreciated, such an approach facilitates an initial establishment of a threaded interconnection between the first thread portions and a collar of a medical-liquid, male connector, followed by the establishment of an enhanced, tight interconnection as the collar is further rotated relative to the second thread portions. As a further option, a raised or protruding stop collar may be provided adjacent to a proximal end of the threads for abutting contact with the collar of a medical-liquid, male connector thereby restricting further relative advancement and indicating to a user that a desired, tight interconnection has been achieved.

In another embodiment, an interconnection surface on a tubular portion may be defined by one or more projecting deformable ribs. The deformable ribs may be oriented at a pitch which is transverse to threads provided on a collar of medical-liquid, male connector, wherein the collar threads cross-over, and thereby depress the ribs as rotative interconnection is established. The deformable ribs are of a sufficiently resilient nature to at least partially return to their initial configuration after depression by the collar threads so as to yield a tight interconnection therebetween.

In another approach, the interconnection surfaces on the docking apparatus and medical-liquid, male connector may comprise one or more projections that are sized/shaped to allow for relative passage past each other upon linear advancement and then to interfere upon relative rotation so as to maintain the medical liquid, male connector in a docked position. In yet another approach, one or both of the interconnection surfaces on the docking apparatus and medical-liquid, male connector may be tapered to facilitate a friction-fit interface therebetween. For example, the interconnection surface of the docking apparatus may define the periphery of the holding member opening and be of a size/shape to slidably receive a tapered nozzle end of a medical-liquid, male connector that is of complimentary size/shape to yield a friction-fit interface.

In a further aspect of the invention, the deformable member may be disposed relative to an interconnection surface on the docking apparatus so that the deformable member is interposed between (e.g. in contact engagement) such interconnection surface and a complimentary interconnection surface of a medical-liquid, male connector during docking use. As such, an antibacterial material applied to an outer surface of the deformable member may (e.g. a top surface of a cap portion of a T-shaped member or of a film member) contact the complimentary interconnection surface during docking. In turn, the maintenance of sterility of a complimentary interconnection surface of a medical-liquid, male connector may be enhanced.

In another aspect, a holding member of the docking apparatus may include at least a first laterally-extending portion that extends away from a tubular portion thereof, wherein the opening of the docking apparatus is located at the top end of the tubular portion. In this regard, the first laterally-extending portion of the holding member facilitates grasping and manipulation of the docking apparatus by the user. In various embodiments, the tubular portion may extend, or protrude, away from the laterally-extending portion in an upstanding manner.

In yet a further independent aspect of the invention, a holding member for a depressible member of a docking apparatus may include a first laterally-extending portion and a second laterally-extending portion, wherein the first and second laterally extending portions may be positioned or positionable in opposing face-to-face relation to retentively engage and be supported by a tubing length therebetween (e.g. a tubing length of a tubing line set present at a patient care site or otherwise provided with an interconnected docking apparatus for use at a patient care site). In this regard, the first and second laterally-extending portions may have coincidental or a mirrored outer surface configurations, wherein a compact docking apparatus is defined when the first and second laterally-extending portions are positioned (e.g. interconnected in face-to-face relation).

In this regard, in one embodiment opposing first edges of the first and second laterally-extending portions may be fixedly interconnected by a hinge. In turn, second side edges of the first and second laterally-extending portions may be provided with the connection members to allow for selective interconnection therebetween.

In one approach, the docking apparatus may be initially provided to users with the first and second laterally-extending portions of the holding member interconnected only along the hinge to define an open clam-shell, or butterfly, configuration with mirrored, opposing halves. In turn, a user may readily position the first and second laterally-extending portions on opposing sides of a tubing length, (e.g. for administration of a medical liquid to a patient) at a patient site and pivot one or both of the first and second laterally-extending portions so that the connection members interconnect along their second side edges so as to retentively attach the docking apparatus to the tubing length. In this regard, the connection members may be provided so that, once connected to a tubing length, the connection members cannot be disconnected from each other, thereby restricting removal of the docking apparatus and possible undesired reuse thereof.

In one embodiment, the first and second laterally-extending portions may be configured to allow for selective, slidable movement along, and yet be retained at a given selected position relative to, a tubing length after interconnection thereto. For example, a tortuous, or serpentine, tubing length path may be defined by internal configurations of the opposing faces of the first and second laterally-extending portions that non-occlusively engage the tubing length. Further, upon interconnection the docking apparatus may be slidably moved to a desired position along the tubing length. The docking apparatus may then maintain such position or may be subsequently slidably moved to another position by a user.

In a related approach, a docking apparatus of the clam-shell configuration noted above may be interconnected (e.g. by connection members) to a tubing length of a tubing line set at a production facility and packaged and shipped to a customer for use at a patient care site. The various features noted above may be utilized with this approach.

In relation to this aspect, a deformable member accessible through an opening may be employed in a tubular portion. For example, the deformable member may comprise a film member or a T-shaped member as described herein. Alternatively, any other known depressible type member positionable within a tubular portion of a docking apparatus may be employed with the described holding member. For example, depressible members may be employed as described in U.S. patent application Ser. No. 10/226,183 entitled "STERILE DOCKING APPARATUS AND METHOD", filed Aug. 22, 2002, the entirety of which is hereby incorporated by reference.

In further conjunction with this aspect, the tubular portion of the holding member that provides the opening for docking may comprise first and second tubular sections, wherein the first laterally-extending portion of the holding member extends laterally away from the first tubular section and the second laterally-extending portion of the holding member extends laterally away from the second tubular section. In this arrangement, the first and second tubular sections are connected to the first and second laterally-extending portions, respectively, so that upon relative pivotal movement and connection between the first and second laterally-extending portions the first and second tubular sections are coaxially aligned to define the tubular portion of the holding member.

In this regard, a depressible member having at least two portions depressible within first and second tubular sections of a tubular portion may be provided. More particularly, the two portions of the depressible member may be configured relative to the first and second tubular sections so that one of the portions is restricted from passage into one of the tubular sections. By way of example, a depressible member having a first portion (e.g. positionable nearest an opening of the tubular portion) with a first maximum cross-dimension (e.g. diameter) and a second portion with a greater, second maximum cross-dimension (e.g. diameter) may be utilized with a tubular portion having a first tubular section (e.g. located nearest the opening) having an inside minimum cross-dimension (e.g. diameter) that is greater than the maximum cross-dimension of the first portion of the depressible member and less than the maximum cross-dimension of the second portion of the depressible member, and a second section having an inside maximum cross-dimension that is greater than the maximum cross-dimension of the second portion of the depressible member. As may be appreciated, such an arrangement facilitates retention of the second portion of the depressible member within the second tubular section.

In one embodiment that comprises first and second laterally-extending portions interconnected to define an open, clam-shell configuration, the depressible member may be defined by a T-shaped deformable member as described herein. In such embodiment, the T-shaped member may be initially disposed so that a first sub-portion of the leg portion thereof is disposed within a first tubular section of a tubular portion, and so that a second sub-portion of the leg portion extends out of and away from the first tubular section. In turn, upon interconnection of the docking apparatus to a tubing length, the second sub-portion of the leg portion of the T-shaped member may pivot into and be received by a second tubular section of the tubular portion that is interconnected to a second laterally-extending portion of the docking apparatus. Again, connection members may be utilized on the first and second laterally-extending portions to maintain the first and second laterally-extending portions in a closed, interconnected state upon a tubing length at a patient care site.

In another aspect, the docking apparatus may further include a flange member interconnected to the holding member and extending laterally away from a tubular portion of the holding member. In one embodiment, at least a portion of the tubular portion of the holding member and at least a portion of a conical, outer surface portion of a film member each at least partially project through an aperture that is provided through the flange member. In turn, an interconnection surface may be provided on the outside surface of the tubular portion to interface with a complimentary interconnection surface of a collar of a medical-liquid, male connector. In such embodiment, it may be preferable for the aperture to be sized to receive a range of outside collar widths utilized on medical-liquid, male connectors, including male luer type connectors.

In conjunction with this embodiment, the holding member may include a laterally-extending portion that extends away from a tubular portion thereof, wherein the laterally-extending portion and a flange member may be adapted for ready interconnection with a peripheral ring portion of the film member captured therebetween. By way of example, a plurality of clip extensions may be provided about a periphery of the flange member for snap-on interconnection of the flange member to a laterally-extending portion of the holding member. As may be appreciated, the inclusion of a flange member and/or a laterally-extending portion of a holding member also facilitates grasping and manipulation of the docking apparatus by a user.

Additional user-friendly features may be included in the inventive docking apparatus. For example, an outer surface portion of the deformable member may be provided in coaxial alignment with the holding member opening and may be presented in a visually distinct manner to facilitate insertion of a nozzle end of a medical-liquid, male connector into the opening. In this regard, such outer surface portion of the deformable member may be provided to correspond in shape with the opening of a holding member. In one approach, a substantially planar or convex, outer surface portion of the film member, and a surrounding (e.g. ring-shaped), conical, outer surface portion of a film member, may be provided to be visually distinct to a user. Similarly, a top surface of a laterally-extending portion of the holding member or of a flange member may be presented to be visually distinct from one or both of the noted surface portions of the film member.

As may be appreciated, an inventive method for docking a medical-liquid, male connector is also provided. The inventive method includes the steps of engaging a nozzle end of a medical-liquid, male connector with an outer surface of a deformable member disposed across an opening of a holding member of a docking apparatus (i.e. by advancing at least one of the medical-liquid, male connector and docking apparatus toward the other), and deforming the deformable member of the docking apparatus to envelop the nozzle end of the medical-liquid, male connector (i.e. by further relative advancement as the nozzle end is inserted through the opening of the holding member of the docking apparatus). In turn, sterility maintenance of the nozzle end of the medical-liquid, male connector is enhanced during docking.

The inventive method may further comprise the step of contacting the outer surface of the deformable member of the docking apparatus with an antibacterial material prior to the engaging and deforming steps. By way of example, the contacting step may entail passing a swab across the outer surface of the deformable member, wherein the swab comprises or has otherwise been contacted with an antibacterial material.

In one characterization, the deforming step may comprise reconfiguring at least a portion of the deformable member from an initial configuration (e.g. a sheet-like or plate-like configuration) to a cup-shaped configuration for isolation of the nozzle end of the medical-liquid, male connector therewithin. In another characterization, the holding member may include a tubular portion that defines the opening, and the deforming step may include positioning a portion of the deformable member over the nozzle end of the medical-liquid, male connector and between a portion of the tubular portion and a distal sidewall portion of the nozzle end of the medical-liquid, male connector.

In one aspect, the inventive method may further include the step of interconnecting the medical-liquid, male connector with the docking apparatus (e.g. in conjunction with or after said deforming step), wherein the nozzle end of the medical-liquid, male connector is maintained in the enveloped position. In relation to the interconnecting step, a distal edge of the nozzle end of the medical-liquid, male connector may be maintained in contact engagement with the outer surface of the deformable member of the docking apparatus (i.e. throughout the interconnecting step). In this manner, the maintenance of sterility is further enhanced.

In this regard, the deformable member may be provided so that an outer surface of the deformable member may apply a predetermined minimum pressure across the entirety of the distal edge of the nozzle end of the medical-liquid, male connector, thereby yielding a pressure seal and hermetic seal during the interconnecting step. Such predetermined pressure may be at least about 1 psi, and preferably between about 1 psi and 6 psi.

The interconnecting step may include the substep of interfacing an interconnection surface on the holding member of the docking apparatus in retentive relation with a complimentary interconnection surface of the medical-liquid, male connector. In one approach, the complimentary interconnection surface on the medical-liquid, male connector may be provided on a rotatable collar thereof, and the interfacing step may entail rotatably advancing the collar of the medical-liquid, male connector relative to the holding member of the docking apparatus (e.g. so as to threadably engage compatible threaded surfaces comprising the respective interconnection surfaces).

In a further aspect, the deformable member may include a T-shaped member having a cap portion that extends over the opening through the holding member and a leg portion that extends through the opening in an initial configuration, wherein the deforming step includes depressing the leg portion of the T-shaped member. In this regard, the cap portion may include a peripheral flap region that extends laterally away from the opening prior to the deforming step, wherein the depressing step comprises drawing the flap region through the opening so that said cap portion assumes a cup-like configuration. In conjunction with this aspect, the method may further include the steps of removing the nozzle end of the medical-liquid, male connector from the opening of the holding member, and utilizing a spring force of the leg portion to urge the cap portion through the opening to reconfigure the cap portion from the cup-shaped configuration to the initial configuration.

In this regard, the peripheral flap region may be of a pliable and resilient nature so that upon removal of the nozzle end of the male connector the flap region engages the inner sidewalls of the tubular portion so as to remove fluid that may have been introduced into the distal end of the tubular portion during docking.

In another aspect, the member may comprise a film member and the deforming step of the inventive method may comprise first and second stages stretching. In the first stage, a film member may be stretched across an area that is larger than the area of the opening of the holding member of the docking apparatus. By way of example, this may be achieved by disposing the film member to extend over and laterally away from one end of the holding member as noted above. In a second stage of the stretching step, the film member is restrainably interposed between complimentary interconnection surfaces of the docking apparatus and medical-liquid, male connector, and therefore stretching of the film member is substantially limited to a smaller area than during the first stage. Providing a larger area for first stage stretching facilitates the maintenance of elastic deformation capabilities of the film member.

In yet a further aspect, the inventive method may include the additional steps of disconnecting the medical-liquid, male connector from the docking apparatus, and disengaging the nozzle end of the medical-liquid, male connector from the surface of the deformable member, wherein the deformable member substantially returns to an initial, pre-docking configuration (i.e. the configuration of the deformable member prior to the initial engaging step). As may be appreciated, the inventive method may further comprise the step of repeating the above-noted engaging, stretching, interconnecting, disconnecting, and disengaging steps a plurality of times. In this manner, it may be appreciated that the inventive method provides for the repeated use of a docking apparatus to maintain the sterility of one or more nozzle end(s) of medical-liquid, male connector(s) over an extended period of use. In an additional independent aspect, the inventive method may include the step of interconnecting a docking apparatus to a tubing length (e.g. a tubing line set utilized) at a patient care site. In this regard, the holding member of the docking apparatus may include first and second laterally-extending portions, wherein the interconnecting step includes positioning the tubing length between the first and second laterally-extending portions, and retentively engaging the tubing length between the first and second laterally-extending portions. In relation to this aspect, the first and second laterally-extending portions may be hingedly connected along opposing first side edge portions and include connection members on second side edge portions. In turn, the engaging step may include pivoting at least one of the second side edge portions of the first and second laterally-extending portions relative to the other so as to interconnect the connection members. Additionally, the engaging step may comprise the step of locking the first and second laterally-extending portions in an interconnected relationship to restrict removal of the docking apparatus from the tubing length.

Additional aspects and advantages of the present invention will be appreciated by those skilled in the art upon further consideration of the description that follows.

DETAILED DESCRIPTION OF THE INVENTION

Figure 3:
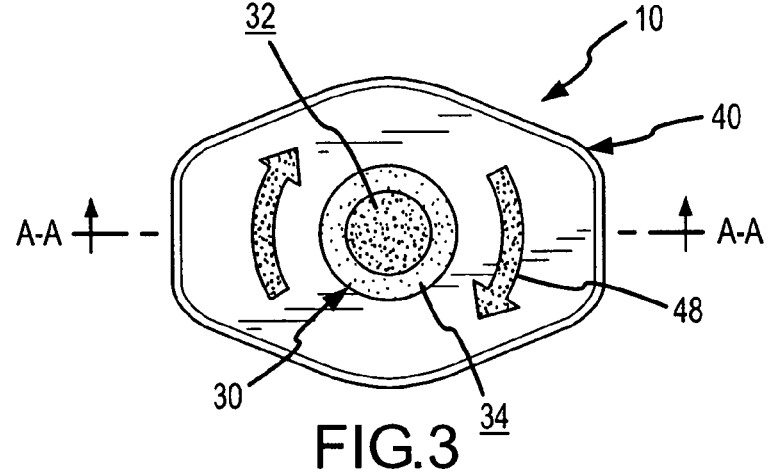
FIG. 3 is a top view of the docking apparatus embodiment of FIGS. 1 and 2.
Figure 4:
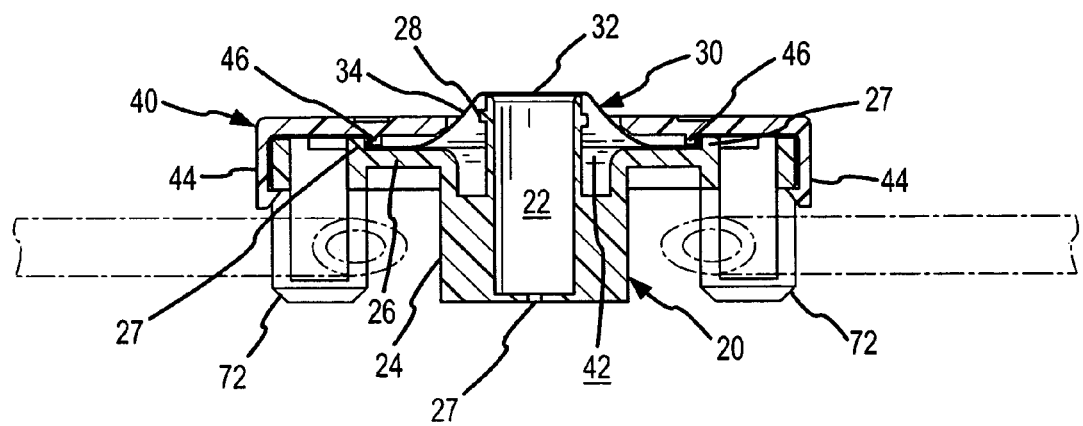
FIG. 4 is a side, cross-sectional view of the docking apparatus embodiment of FIGS. 1-3, taken along section line AA of FIG. 3.
Figure 5:
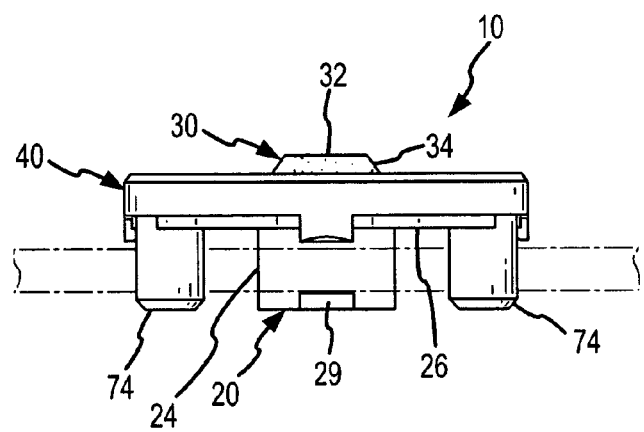
FIGS. 5 and 6 illustrate side and end views, respectively, of the docking apparatus embodiment of FIGS. 1-4.
Figure 6:
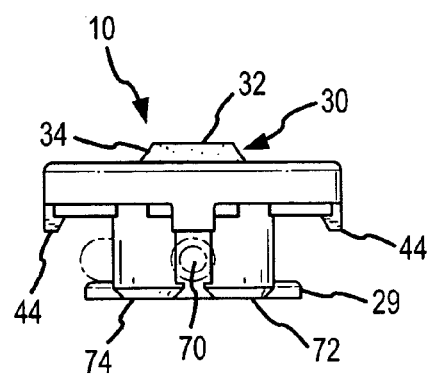

FIGS. 1-6 illustrate one embodiment of a medical-liquid, male connector docking apparatus 10 comprising the present invention. As best shown by FIG. 4, the docking apparatus 10 includes a holding member 20 having an opening 22 and a deformable member comprising a stretchable, sheet-like film member 30 disposed across the opening 22. The stretchable nature of film member 30 facilitates the isolation of a nozzle end of a medical-liquid, male connector that is inserted into the opening 22 by responsively stretching to envelop the nozzle end in a tent-like manner. By virtue of such isolation, maintenance of the sterility of a nozzle end of a medical-liquid, male connector may be enhanced.

Preferably the film member 30 is not only stretchable, but is also elastic, wherein the film member 30 is able to elastically deform during use and substantially return to its initial configuration after removal of a nozzle end of medical-liquid, male connector from opening 22. Further, an elastic film member 30 may advantageously, apply a predetermined minimum pressure (e.g. at least 1 psi, and preferably 1 psi to 6 psi) across a nozzle end of a medical-liquid, male connector during docking. For example, film member 30 may comprise a polymer-based material such as the material selected from a group comprising: thermoset rubbers and thermoplastic polyurethanes.

In preferred arrangements, film member 30 may be of a substantially uniform thickness. By way of example, such thickness may be at least about 0.006 in., and preferably between about 0.006 in. and 0.009 in.

The film member 30 may be provided to define a continuous, substantially planar surface portion 32 that extends across and coincides with the shape of the opening 22, thereby facilitating the application of an antibacterial material thereto prior to being engaged by the distal edge of a nozzle end of a medical-liquid, male connector. In turn, contact engagement across the distal edge of a nozzle end of a medical-liquid, male connector is enhanced. Further, the provision of a continuous surface portion facilitates the avoidance of fluid retention thereupon after the film member 30 returns to its initial configuration after docking. To yield such an arrangement, film member 30 may extend over the opening 22 in co-planar relation to a periphery of the opening 22, as shown in FIG. 4.

Of further note, it may be desirable for the film member 30 to comprise an antibacterial material such as metal ions (e.g. silver salts such as sulfadiazine). As may be appreciated, the utilization of a film member 30 comprising an antibacterial material further enhances the maintenance of sterility upon contact engagement with a nozzle end of a medical-liquid, male connector.

The holding member 20 may include a tubular portion 24, wherein the opening 22 is located at a top end of the tubular portion 24. In the illustrated embodiment, the holding member 20 further comprises a laterally-extending portion 26 extending away from the tubular portion 24. Further, the docking apparatus 10 includes a flange member 40 extending away from the tubular portion 24 and interconnected to the laterally-extending portion 26 of the holding member 20. The provision of laterally-extending portion 26 and/or flange member 40 provides a structure that may be readily grasped by a user for use and manipulation of the docking apparatus 10.

The top end of the tubular portion 24 of the holding member 20 projects through and away from an aperture 42 provided through the flange member 40. Preferably the aperture 42 has a diameter of at least about 0.375 in., and even more preferably between about 0.4375 in. and 0.75 in.

The film member 30 is disposed over the top end of the tubular portion 24 of the holding member 20 and captured between the laterally-extending portion 26 of the holding member 20 and the flange member 40, wherein the film member 30 defines a continuous, frusto-conical, outer surface that also projects outward from the flange member 40. That is, the frusto-conical surface includes the above-noted planar surface portion 32, and a surrounding, ring-shaped, conical surface portion 34. As may be appreciated, the frusto-conical, outer surface may be readily contacted with an antibacterial material prior to the insertion of a nozzle end of a medical-liquid, male connector through the opening 22 of the docking apparatus 10.

To provide for retentive engagement between the docking apparatus 10 and a medical-liquid, male connector, an interconnection surface 28 may be provided on the tubular portion 24 of holding member 20. More particularly, the interconnection surface 28 may be adapted to interface with a complimentary interconnection surface provided on a medical-liquid, male connector, wherein the film member 30 is interposed between the interconnection surface 28 of the docking apparatus 10 and the interconnection surface of a medical-liquid, male connector during docking use.

In the illustrated embodiment, interconnection surface 28 comprises a threaded surface on an outer surface of tubular portion 24 that may interface with a complimentary, threaded interconnection surface on the inside of a collar of a medical-liquid, male connector. In turn, the ring-shaped, conical surface 34 of film member 30 may be restrainably engaged between the two interconnection surfaces during docking. As shown, the frusto-conical surface of film member 30 is provided so as to extend over and about the interconnection surface 28 prior to docking use.

To accommodate stretching of the film member 30 during interconnection of the docking apparatus 10 with a medical-liquid, male connector, the threads of interconnection surface 28 in the illustrated embodiment may be rounded. Further, the distal end of the threads of interconnection surface 28 may be set back a distance from the distal end of the tubular portion 24. Additionally, it may be preferable to provide for a predetermined clearance between the threaded interconnection surface 28 and complimentary threaded interconnection surface of a medical-liquid, male connector. In particular, a predetermined clearance of at least 2 times the thickness of film member 30 is preferred. In addition, it may be preferable for the periphery of opening 22 of a holding member 20 to provide a clearance relative to a docked nozzle end of a medical-liquid, male connector of at least 2 times the thickness of film member 30.

To facilitate the interconnection of the holding member 20 and flange member 40, flange member 40 may be provided with a plurality of clip extensions 44 about its periphery. Such clip extensions 44 are sized/shaped to extend around a peripheral edge of the laterally-extending portion 26 of the holding member 20 and retainably engage the underside thereof in a snap-on-like manner. In this regard, it may be appreciated that the assembly of docking apparatus 10 may be completed in a relatively simple manner.

For example, film member 30 may be sized/shaped slightly larger than the top aspect of holding member 20 and positioned over the holding member 20. Next, the flange member 40 may be advanced relative to the holding member 20 with the film member 30 captured therebetween. In this regard, the flange member 40 may be provided with an annular, downward-facing ring 46 that may be adjacently located within a concentric, upward-facing annular ring 27 provided on the laterally-extending portion 26 of the holding member 20, wherein the film member 30 is secured therebetween about a ring-shaped region. As may be appreciated, the film member 30 is operative to stretch across the area that is within the ring-shaped region. Further, the film member may be slightly tensioned upon assembly.

Figure 1:
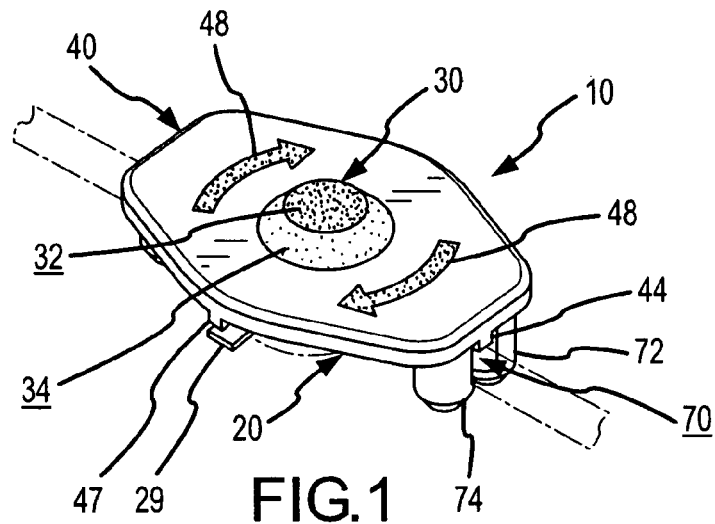
FIGS. 1 and 2 are perspective views of a top side and bottom side, respectively, of one docking apparatus embodiment of the present invention.
Figure 2:
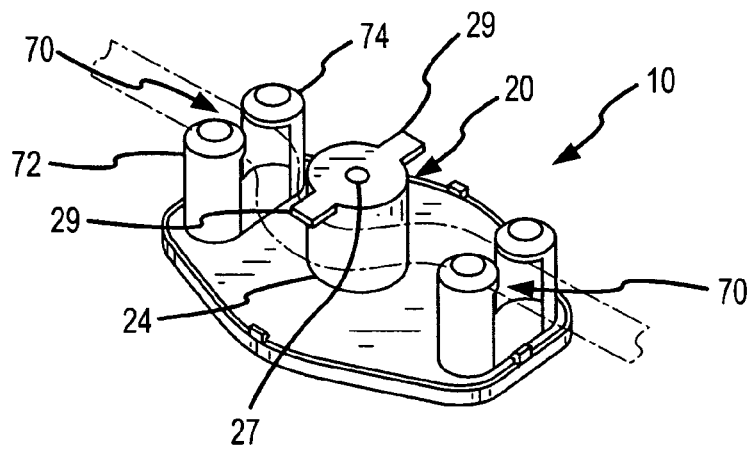

Referring now to FIGS. 1 and 3, a number of features may be noted that facilitate docking of a medical-liquid, male connector. First, the planar surface portion 32 of film member 30 and the surrounding, ring-shaped, conical surface portion 34 may be provided to be visually distinct from each other, as well as visually distinct from a top surface 46 of the flange member 40. That is, all or adjacent ones of the planar surface portion 32, ring-shaped, conical surface portion 34 and top surface 46 may be of a different hue or color so as to present a target-like appearance to a user. Further, directional indicia 48 may be provided on the top surface of the flange member 40 so as to facilitate interconnection of the docking apparatus 10 and a medical-liquid, male connector. For example, directional arrows may be presented in a visually distinct manner to indicate the rotational direction that a collar of a medical-liquid, male connector should be turned (e.g. clockwise) relative to docking apparatus 10 in order to achieve a threaded interconnection therebetween.

To further facilitate the use of docking apparatus 10, holding member 20 may be provided with a reduced passageway 27 at the bottom end of the tubular portion 24. Such reduced passageway allows air and liquid to exit from within the holding member 20, yet restricts a user from attempting to dock a medical-liquid, male connector at the wrong end of tubular portion 24.

As illustrated by FIGS. 1, 2, and 4-6, docking apparatus 10 may include a number of slots 70 that are sized and located to selectively receive a medical liquid tubing line, (shown in phantom). For example, slots 70 may be provided between legs 72, 74 that extend away from the laterally-extending portion 26 at opposing ends of the docking apparatus 10. In this regard, each pair of legs 72, 74 may be spaced a distance that is slightly less than the diameter of a typical medical liquid tubing line used in a patient care facility (e.g. about $\frac{1}{16}$-$\frac{3}{16}$") so as to facilitate, retentive engagement of the docking apparatus 10 relative to such tubing line. Further, by routing a tubing line between slots 70 and about the outside of the tubular portion 24 of the holding member 20, a tortuous path is defined, thereby further enhancing retentive placement. Retentive engagement of docking apparatus 10 with a tubular line is even further enhanced by the provision of sideward extending tabs 29 at a bottom end of tubular portion 24 of the holding member 20.

Figure 7A:
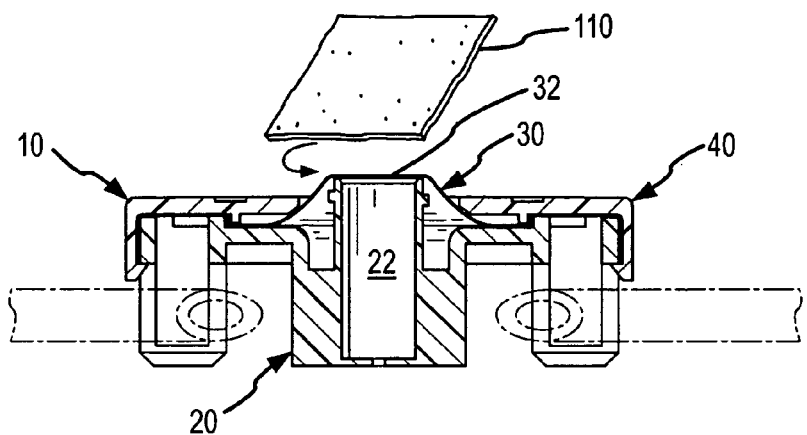
FIGS. 7A, 7B, 7C, 7D and 7E are side, cross-sectional views illustrating the use of the docking apparatus embodiment of FIGS. 1-6 with an exemplary medical-liquid, male connector.
Figure 7B:
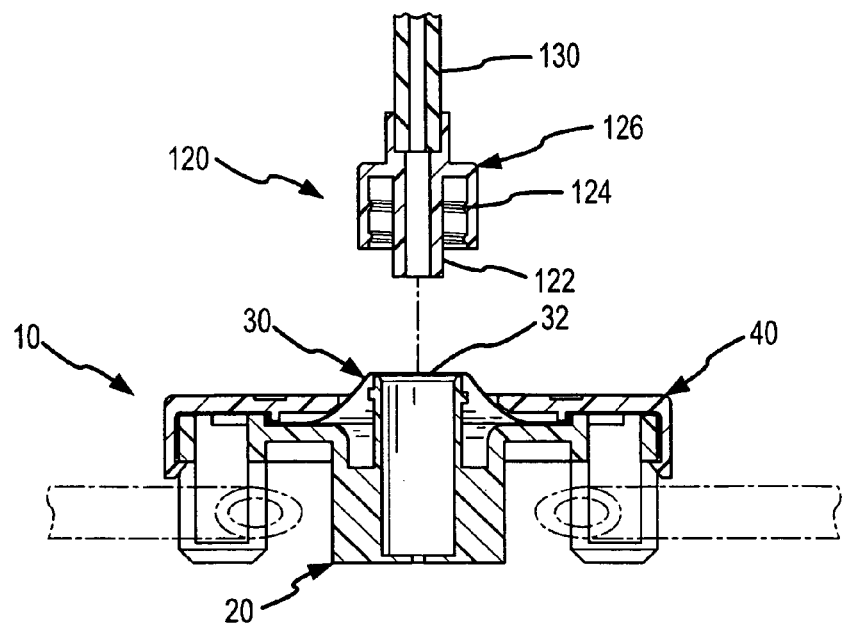

FIGS. 7A-7E illustrate an exemplary use of docking apparatus 10. As shown in each of the figures, the docking apparatus 10 may be interconnected to an exemplary tubing line (shown in phantom) prior to, during or after use of the docking apparatus. As illustrated by FIG. 7A, prior to docking an antibacterial material may be applied to the frusto-conical surface of the film member 30 using a swab 110. Then, as shown FIG. 7B, an exemplary medical-liquid, male connector 120, that is interconnected or interconnectable via a tubing line 130 with a medical liquid source, may be located in an aligned position with the opening 22 of docking apparatus 10. In this regard, and as noted above, a nozzle end 122 of the medical-liquid, male connector 120 may be visually aligned with the visibly distinct, planar surface portion 32 of film member 30. To initiate docking, the medical-liquid, male-connector 120 and/or docking apparatus 10 may be advanced so that the distal of nozzle end 122 of the medical-liquid, male connector 120 engages the planar surface portion 32 and the antibacterial material applied thereto.

Figure 7C:
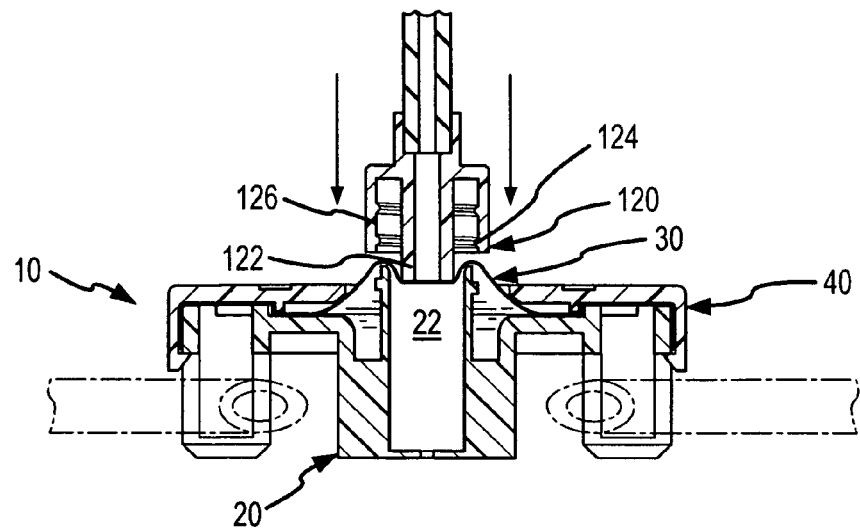

In FIG. 7C, as the nozzle end 122 of the medical-liquid, male connector 120 has engaged the planar surface portion 32 of the film member 30 and begun to stretch the film member 30 into the top end of the tubular portion 24 of the holding member 20. In this regard, it should be noted that during this first stage of stretching, the film member 30 advantageously stretches across an area whose periphery is defined by the interface of annular ring 27 on holding member 20 and annular ring 46 on flange member 40. Such an arrangement facilitates repeated use of the docking apparatus 10 by reducing the likelihood of elastic deformation of film member 30.

Figure 7D:
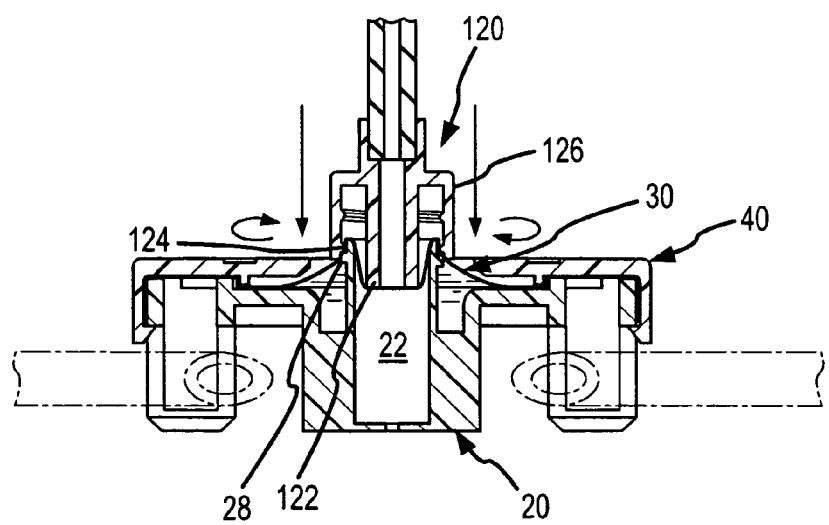

In FIG. 7D, the docking apparatus 10 and/or medical-liquid, male connector 120 has been further advanced, wherein film member 30 has been further stretched inward into the tubular portion 24. Of note, threaded interconnection surface 124 on the inside surface of collar 126 of the medical-liquid, male connector 120 has interfaced with the threaded interconnection surface 28 provided on tubular portion 24 of the holding member 20. As such, upon relative rotation the two interconnection surfaces will restrainably engage the film member 30 therebetween. In turn, further stretching of film member 30 during a second stage will be substantially limited to the area of film member 30 that is located within the restricted region.

Figure 7E:
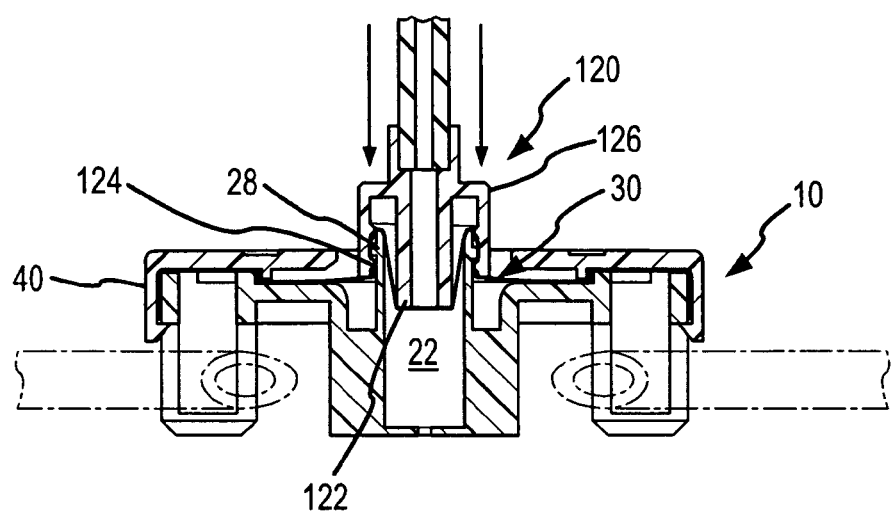

As shown in FIG. 7E, the collar 126 of the medical liquid, male-connector 120 has been rotated relative to the docking apparatus 10 so as to yield threaded engagement and relative advancement. Concomitantly, the nozzle end 122 of the medical liquid, male-connector 120 has been further advanced into the tubular portion 24 of the holding member 20, thereby further stretching film member 30. As may be appreciated, the medical-liquid, male connector 120 may be maintained in the docking position shown in FIG. 7E, wherein maintenance of the sterility of nozzle end 122 and the inside surface of collar 126 is enhanced. Subsequently, the medical-liquid, male connector 120 may be disconnected from docking apparatus 10 by rotating collar 126, wherein film member may elastically return to substantially the same configuration shown in FIG. 7A. Thereafter, the docking apparatus 10 may be repeatedly used as described in relation to FIGS. 7A-7E over an extended period of patient treatment.

FIGS. 8A-8E illustrate another embodiment of a docking apparatus 100, as employed in conjunction with another medical-liquid, male connector 220. The docking apparatus 100 is of the same configuration as docking apparatus 10 illustrated in FIGS. 1-6 and 7A-7E, with the exception that it comprises an interconnection surface 102 that is located on the inside of tubular portion 24, as opposed to an interconnection surface on the outside of the tubular portion 24 as per the prior embodiment. Relatedly, the medical-liquid, male connector 220 is of the same configuration as the medical-liquid, male connector 120 illustrated in FIGS. 7B-7E, with the exception that medical-liquid, male connector 220 does not include an outer collar as per the prior embodiment. Further, the nozzle end 122 of the medical-liquid, male connector 220 includes an outer interconnection surface 224.

As will be appreciated, the interconnection surface 102 of docking apparatus 100 and interconnection surface 224 of medical-liquid, male connector 220 are sized and shaped for retentive interconnection. More particularly, in the illustrated arrangement, the interconnection surfaces 102 and 224 comprise complimentary threaded surfaces. In other arrangements, interconnection surface 224 could be modified to be a tapered outer surface on nozzle end 122 and interconnection surface 102 could be modified to be of a size/shape to slidably receive the tapered outer surface on nozzle end 122 so as to yield a friction-fit interface with film member 30 interposed therebetween.

Figure 8A:
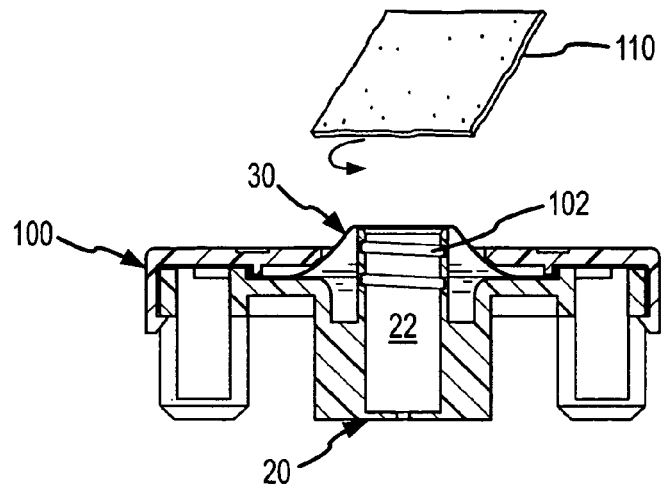
FIGS. 8A, 8B, 8C, 8D, and 8E are side, cross-sectional views illustrating the use of another docking apparatus embodiment with another medical-liquid, male connector.
Figure 8B:
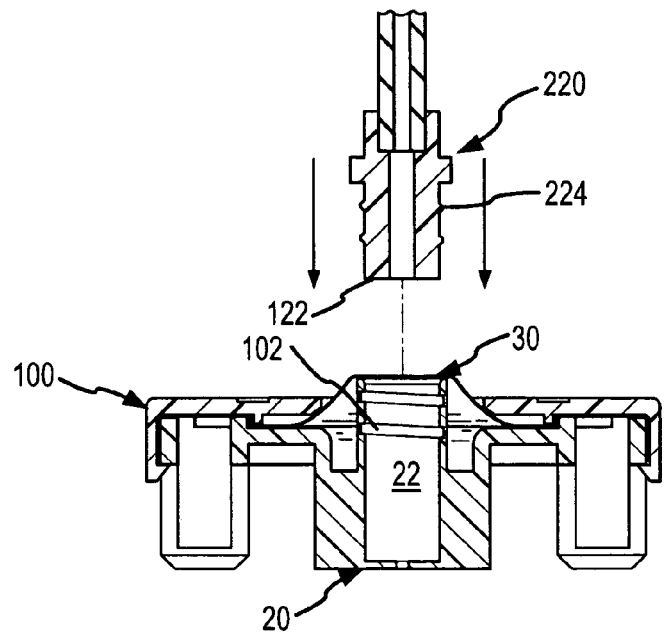

As illustrated by FIG. 8A, prior to docking an antibacterial material may be applied to the frusto-conical surface of the film member 30 using a swab 110. Then, as shown in FIG. 8B, a medical-liquid, male connector 220, interconnected or interconnectable via tubing line 130 with a medical liquid source, may be located in an aligned position with the opening 22 of docking apparatus 100. Again, nozzle end 122 of the medical-liquid, male connector 220 may be visually aligned in co-axial relation with the visibly distinct, planar surface portion 32 of the film member 30. To initiate docking, the medical-liquid, male connector 220 and/or docking apparatus 100 may be advanced so that the distal edge of the nozzle end 122 of the medical-liquid, male connector 220 engages the planar surface portion 32 and the antibacterial material applied thereto.

Figure 8C:
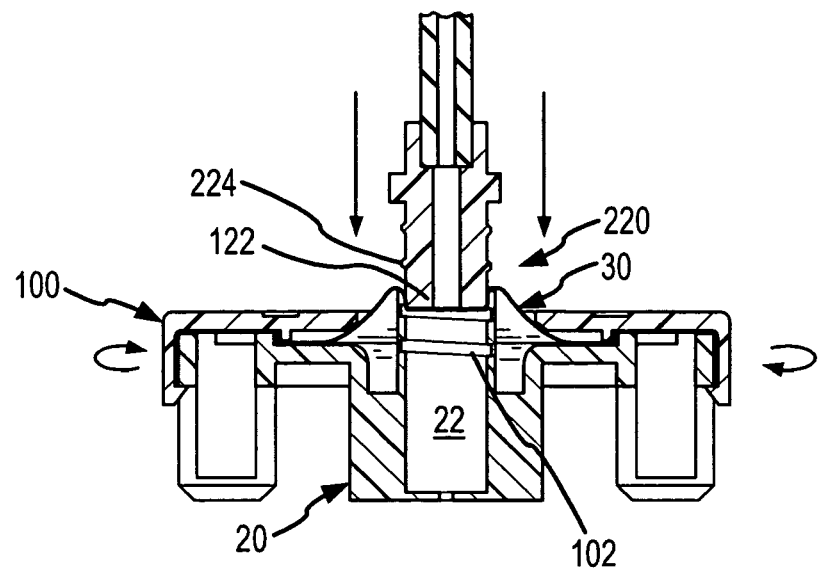

In FIG. 8C, the nozzle end 122 of the medical-liquid, male connector 220 has engaged the planar surface portion 32 of the film member 30 and begun to stretch the film member 30 into the top end of the tubular portion 24 of the holding member 20. Again, it should be noted that during this first stage of stretching the film member 30 advantageously stretches across an area that is greater than the size of the opening 22 of the tubular portion 24 of the holding member 20.

Figure 8D:
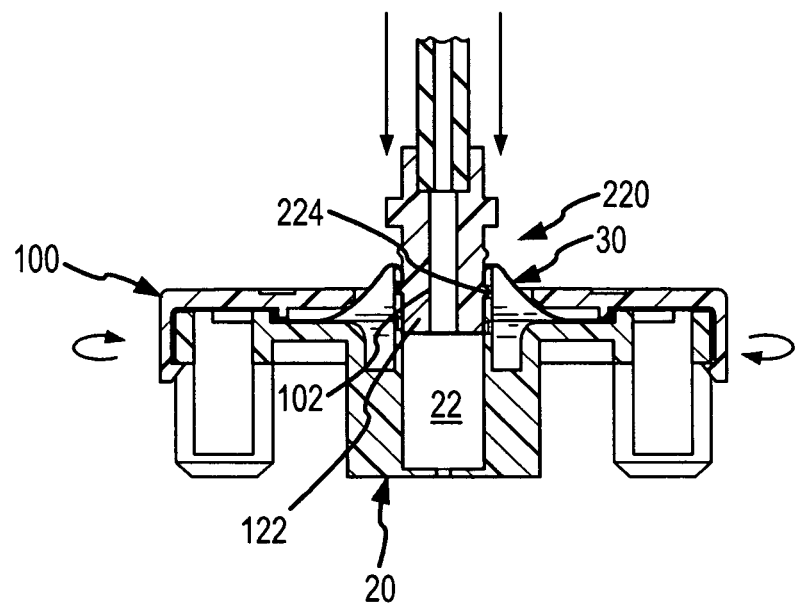

In FIG. 8D, the docking apparatus 100 and/or medical-liquid, male connector 220 has been further advanced. As shown, the threaded interconnection surface 224 on the outside of the nozzle end 122 of the medical-liquid, male connector 220 has begun to interface with the threaded interconnection surface 102 provided on the inside of tubular portion 24 of the holding member 20. As such, upon rotation of the docking apparatus 100 relative to medical-liquid, male connector 220, further stretching of the film member 30 during a second stage will be substantially limited to the area of the film member 30 that is located within the restrained region.

Figure 8E:
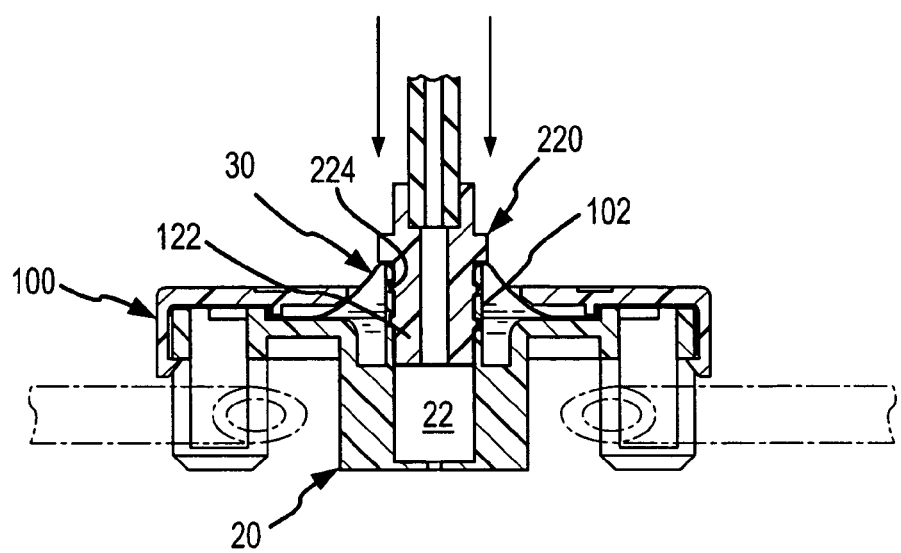

As shown in FIG. 8E, the docking apparatus 100 has been rotated relative to the medical-liquid, male connector 220 so as to yield threaded, retentive engagement. Concomitantly, the nozzle end 122 of the medical-liquid, male connector 220 has been further advanced into the tubular portion 24 of the holding member 20, thereby further stretching film member 30. The medical-liquid, male connector 220 may be maintained in the docking position shown in 8E, wherein maintenance of the sterility of nozzle end 122 and the interconnection surface 224 of nozzle end 122 is enhanced. Subsequently, the medical-liquid, male connector may be disconnected from docking apparatus 100 by rotating during apparatus 100, wherein film member 30 may elastically return to substantially the same configuration shown in FIG. 8A. Thereafter, the docking apparatus 100 may be repeatedly used as described in relation to FIGS. 8A-8E.

Figure 9A:
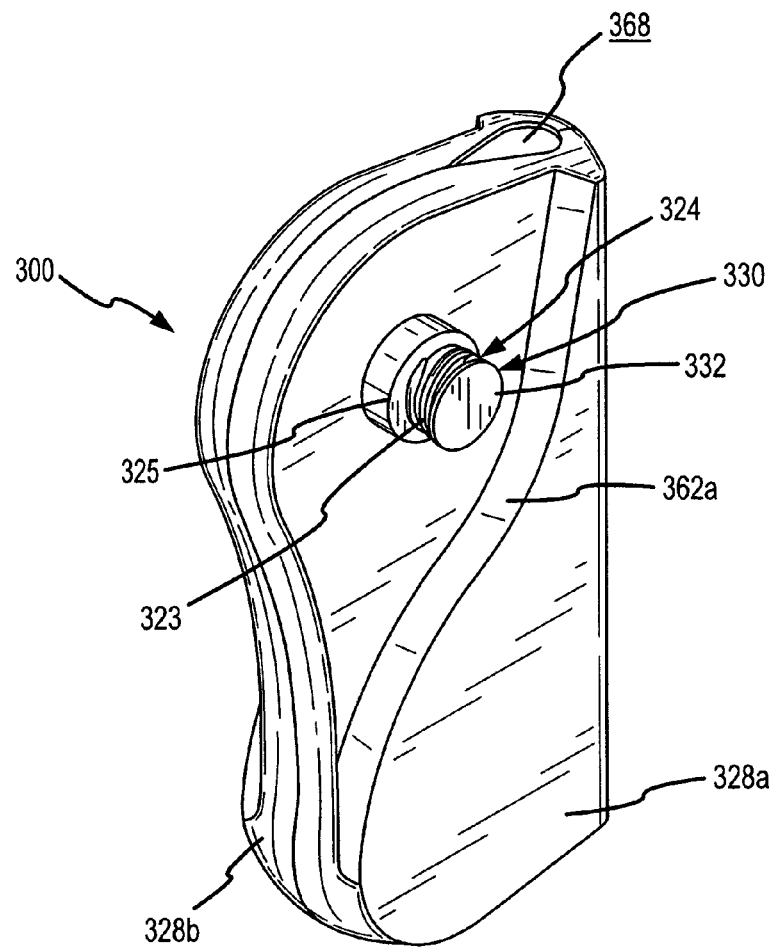
FIGS. 9A, 9B, 9C, 9D, 9E, 9F and 9G illustrate perspective, first side edge, second side edge, top edge, bottom edge, front and rear views, respectively, of another docking apparatus embodiment comprising the present invention.
Figure 9B:
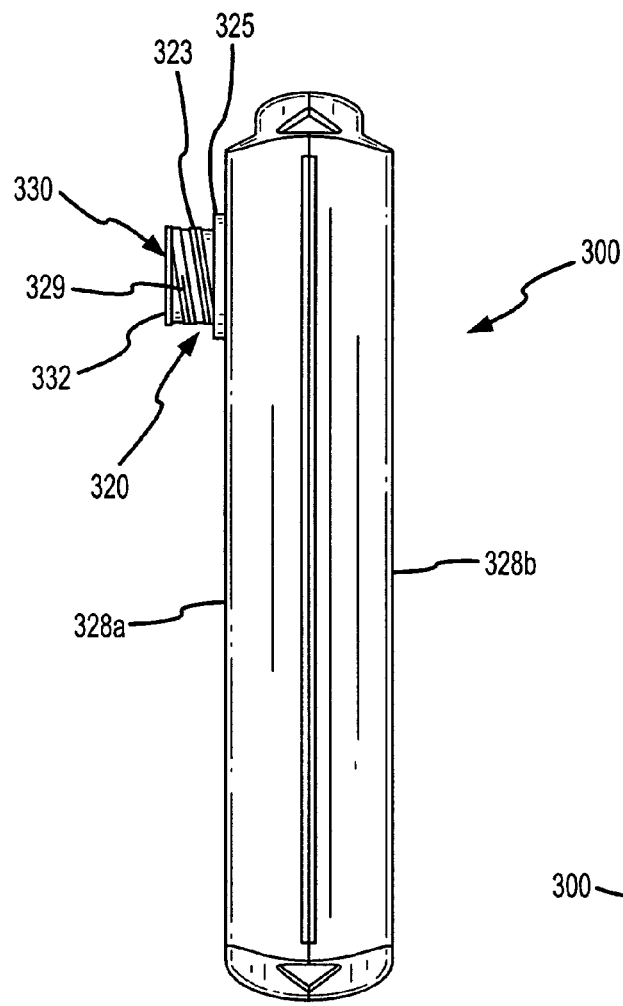
Figure 9C:
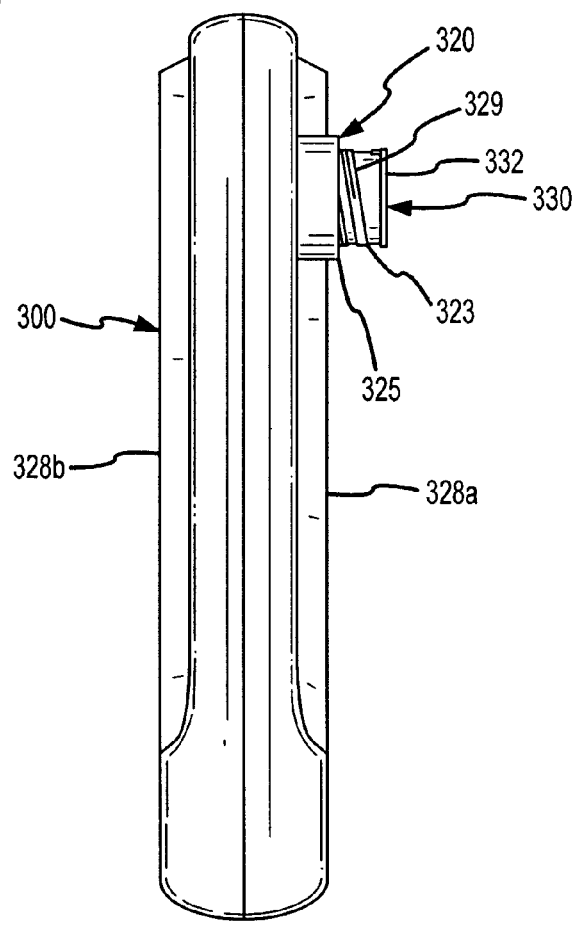
Figure 9D:
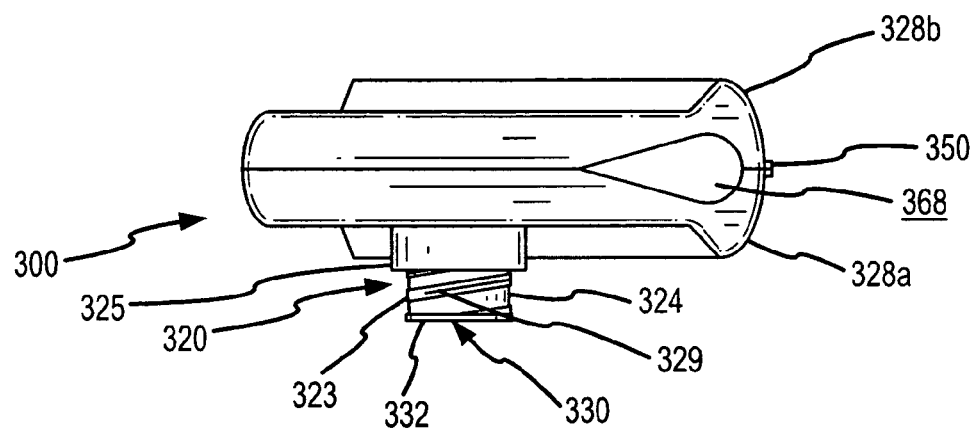
Figure 9E:
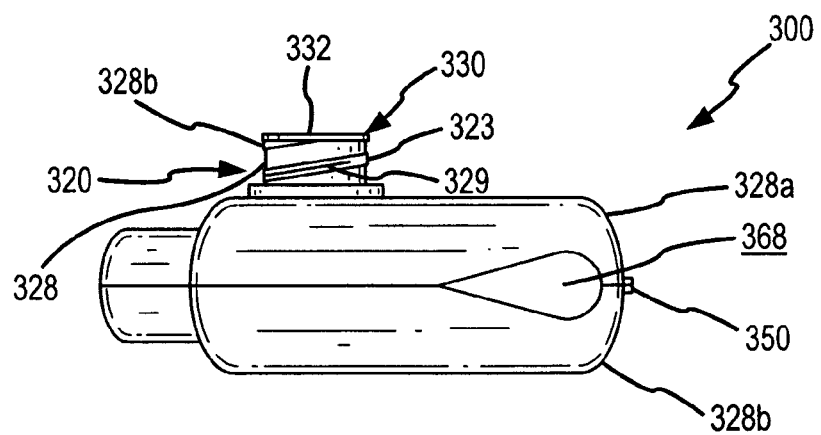
Figures 9F, 9G:
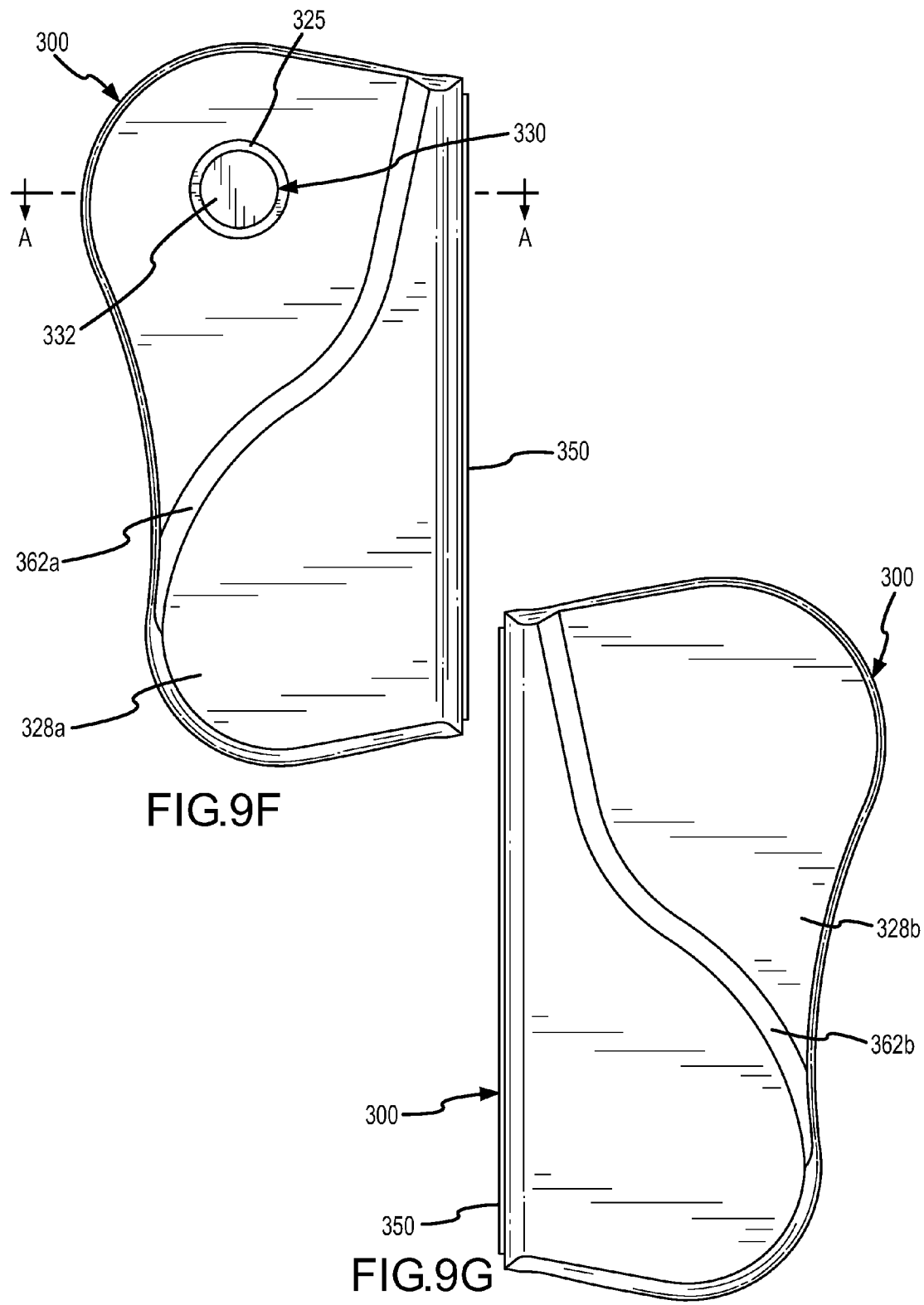
Figure 10:
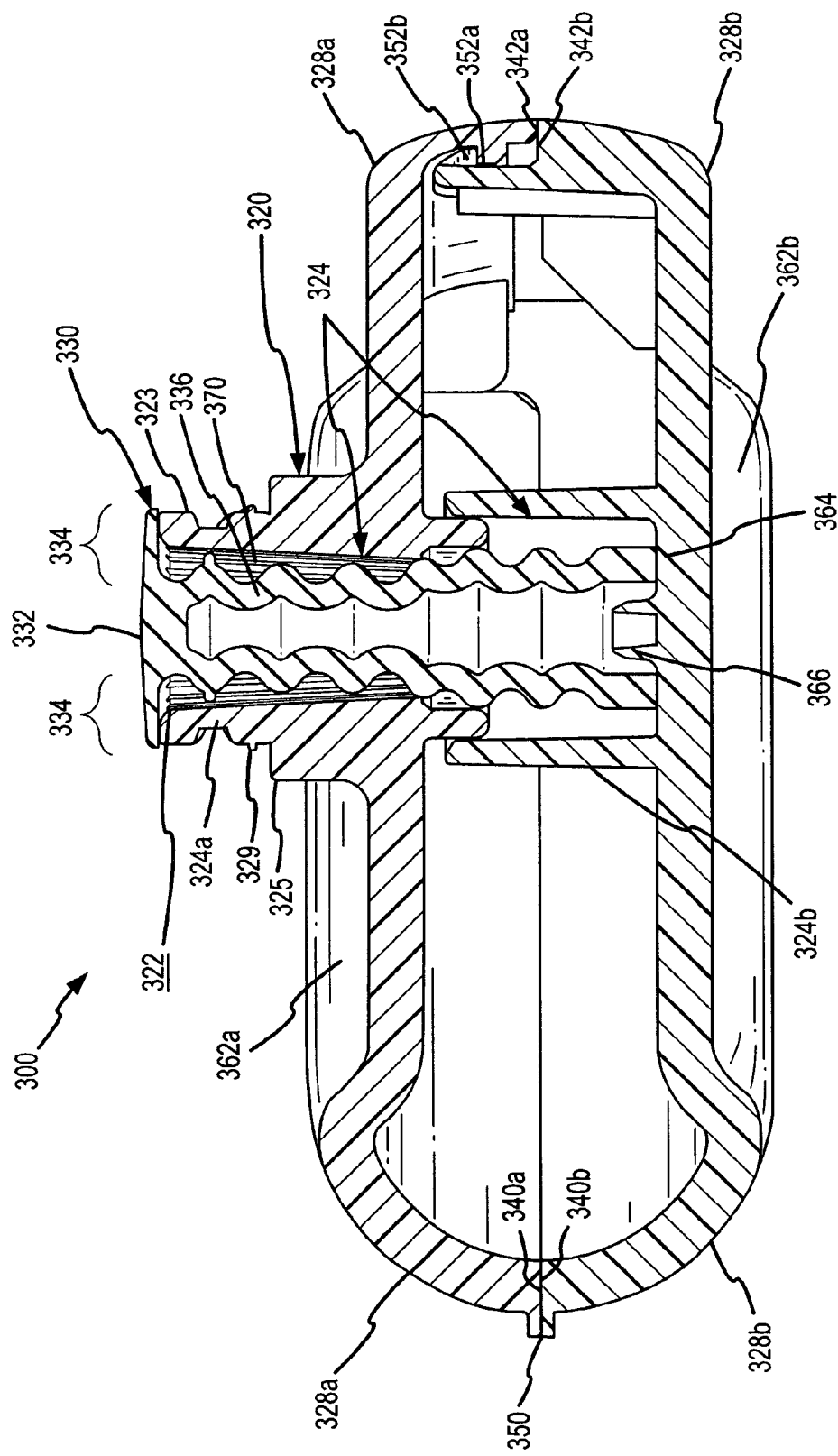
FIG. 10 is a side, cross-sectional view of the docking apparatus embodiment of FIGS. 9A-9G, taken along section line AA of FIG. 9F.

FIGS. 9A-9G, 10, 11A-11B, 12, 13, 14A-14F, and 15 illustrate yet another embodiment of a medical-liquid, male connector docking apparatus 300 comprising the present invention. As best shown by FIG. 10, the docking apparatus 300 includes a holding member 320 having an opening 322 and deformable member defined by a resilient, T-shaped member 330 disposed across and through the opening 322. More particularly, a cap portion 332 of the T-shaped member 330 may be disposed across the opening 322 at one end of a tubular portion 324 of the holding member 320, and an adjoining, resilient leg portion 336 of the T-shaped member 330 may extend through the opening 322 into the tubular portion 324. Of note, the cap portion 332 includes a resilient, peripheral ring, or flap region 334 that extends laterally away from the periphery of the opening 322 and a top end of the leg portion 336. The flap region 334 of the cap portion 332 of the T-shaped member 330 is pliable to facilitate the isolation of a nozzle end of a medical-liquid, male connector that is inserted into the opening 322, e.g. by responsively deforming to yield a cup-shaped configuration of cap portion 332 so as to envelop the nozzle end in a tent-like manner. By virtue of such isolation, maintenance of the sterility of the nozzle end of a medical-liquid, male connector may be enhanced. Further due to the resilient, spring-like nature of the leg portion 336, the cap portion 332 may advantageously apply a predetermined minimum pressure (e.g. at least 1 psi, and preferably 1 psi to 6 psi) to and across the lateral extent of a nozzle end of medical-liquid, male connector during docking, thereby yielding a pressure and hermetic seal.

In order to facilitate the realization and maintenance of a docking relationship, the tubular portion 324 of the holding member may comprise an interconnection surface 323 adapted for retentive engagement with a complimentary surface of a male connector. In the illustrated embodiment, the interconnection surface 323 is defined by dual arcurate threads provided on an outside surface of tubular portion 324. More particularly, dual threads 323 are offset about 180° and each extend around the tubular portion 324 90° to 360° (e.g. about 340° in the illustrated embodiment). As shown, each of the threads 323 may include a first portion that extends around the tubular portion 324 45° to 180° (e.g. about 170° in the illustrated embodiment), and a second portion that extends around the tubular portion 324 45° to 180° (e.g. about 170° in the illustrated embodiment). The second portions of each thread 323 include a further raised rib 329 to facilitate secure interconnection to a male connector. In this regard, a collar of a medical-liquid, male connector may be readily rotated relative to the first portions of threads 323 of docking apparatus 300 to achieve an initial interconnection, then further rotated with increasing resistance relative to the second portions of threads 323 (e.g. thereby engaging raised ribs 329) to achieve a further retentive, tight interconnection to the docking apparatus. Of further note, a stop collar 325 may be provided adjacent to the end of the second portions of threads 323 to provide a user with affirmative touch-feedback as to when a desired, secure interconnection has been realized.

In another embodiment, the interconnection surface 323 may be defined by threads provided on an inside surface of tubular portion 324 at a top end thereof, e.g. for use analogous to that described in relation to FIGS. 8A-8E above. In yet another embodiment, the interconnection surface 323 may be defined by at least one and preferably a plurality of depressible raised ribs disposed on an outside surface of the tubular portion 324. For example, a plurality of depressible raised ribs may be spaced about the tubular portion 324 and provided to progressively depress and reassume their shape as threads of a collar of a medical-liquid, male connector crossover the ribs as the collar is advanced retracted relative thereto. Such depressible ribs may be as described in U.S. patent Ser. No. 10/226,599, entitled "IMPROVED PROTECTIVE CAP AND CAPPING METHOD FOR MEDICAL MALE LUER FITTINGS", filed Aug. 22, 2002 the entirety of which is hereby incorporated by reference.

Due to the resilient nature of the T-shaped member 330, the T-shaped member is able to deform from its initial components of configuration shown in FIG. 10, to a deformed configuration during docking use, and then substantially return to its initial configuration after removal of a nozzle end of a medical-liquid, male connector from opening 322. More particularly, and as will be further described, the leg portion 336 of the T-shaped member 330 may be depressed within a tubular portion 324 of the holding member 320 during docking use, thereby drawing the flap region 334 of the cap portion 332 of the T-shaped member 330 through the opening 322 and into the tubular portion 324 of the holding member 320, wherein the cap portion 332 defines a cup-shaped, or U-shaped configuration.

In this regard, it should be noted that in the illustrated embodiment the leg portion 336 is of a tubular configuration and comprises a plurality of undulations. Such undulations facilitate depression of the leg portion 336 within the tubular portion 324 during docking, and further facilitate spring-back after docking so as to force the cap portion 332 of the T-shaped member 330 back through the opening 322 to assume its initial configuration.

By way of example, both the cap portion 332 and leg portion 336 of the T-shaped member 330 may comprise a polymer-based material such as a synthetic rubber material selected from a group comprising:

Biocompatible silicones;
Polyisoprene rubbers; and
Ethyl-diene-propylene-monomer (EPDM).

In one embodiment, the cap portion 332 and leg portion 336 may be integrally molded from a polymer-based material selected from the noted group. In other arrangements, a polymer-based cap portion 332 may be bonded to a depressible leg portion 336 comprising an open or closed cell foam material.

In yet other arrangements, a polymer based cap portion 332 may be interconnectable to a metal spring comprising leg portion 336.

As illustrated in the illustration in FIG. 10 arrangement, the cap portion 332 of the T-shaped member 330 may be of a substantially uniform thickness. By way of example, such thickness may be at least about 0.06 in., and preferably between about 0.04 in. and 0.07 in. In this regard, and as best shown in FIGS. 9A and 9B, the cap portion 332 of the T-shaped member 330 may be provided to present a continuous, substantially planar or convex, and less preferably, concave, surface portion that extends over and coincides with the shape of the opening 322, thereby facilitating the application of an antibacterial material thereto prior to being engaged by the distal edge of a nozzle end of a medical-liquid, male connector. In turn, contact engagement across the distal edge of medical-liquid, male connector is enhanced. To yield such an arrangement, the cap portion 332 may extend over the opening in co-planar relation to a periphery of the opening 322, as shown in FIG. 10. As further illustrated, the peripheral rim, or flap region 334 of the cap portion 332 extends laterally beyond the entire periphery of the opening 322. In one arrangement, a raised pimple may be provided at the center of a top surface of the cap portion 332. Such pimple may be sized for receipt within the nozzle end of a medical-liquid, male connector.

Of additional note, it may be desirable for at least the cap portion 332 of the T-shaped member 330 to comprise an antibacterial material such as metal ions (e.g. silver salts such as sulfadiazime). The utilization of an antibacterial material further enhances the maintenance of sterility upon contact engagement with a nozzle end of a medical-liquid, male connector.

Figure 11A:
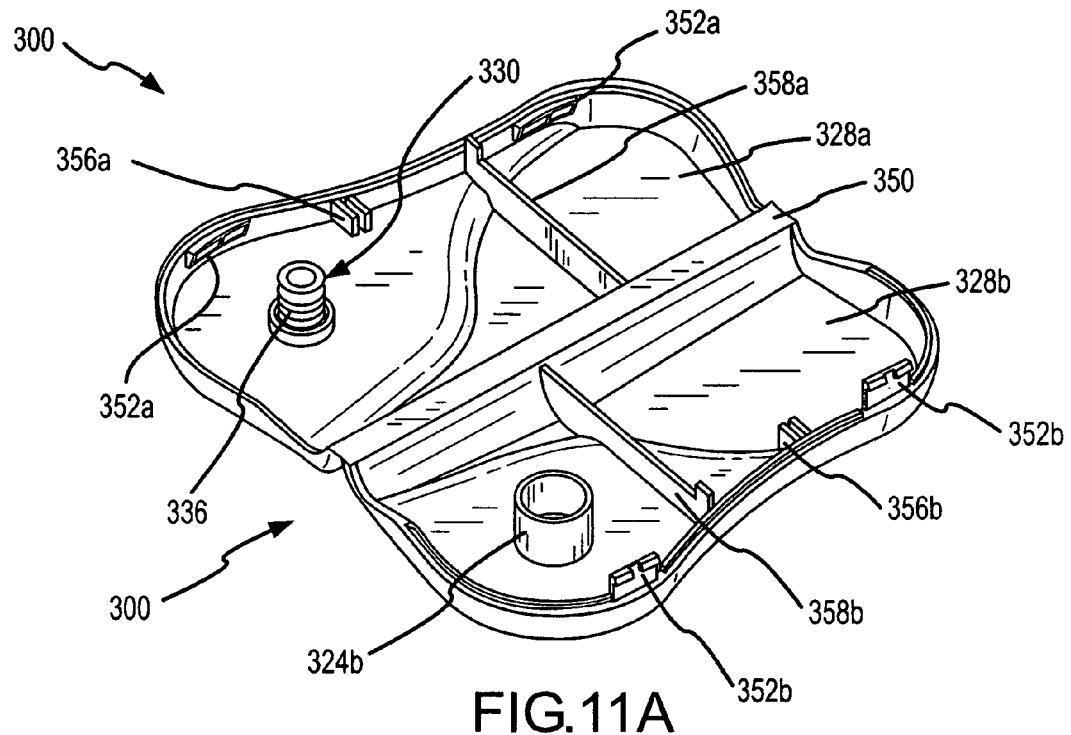
FIGS. 11A and 11B illustrate perspective top and bottom views, respectively, of the docking apparatus embodiment of FIGS. 9A-9G in open position (e.g. prior to retentive closure upon a tubing length).
Figure 11B:
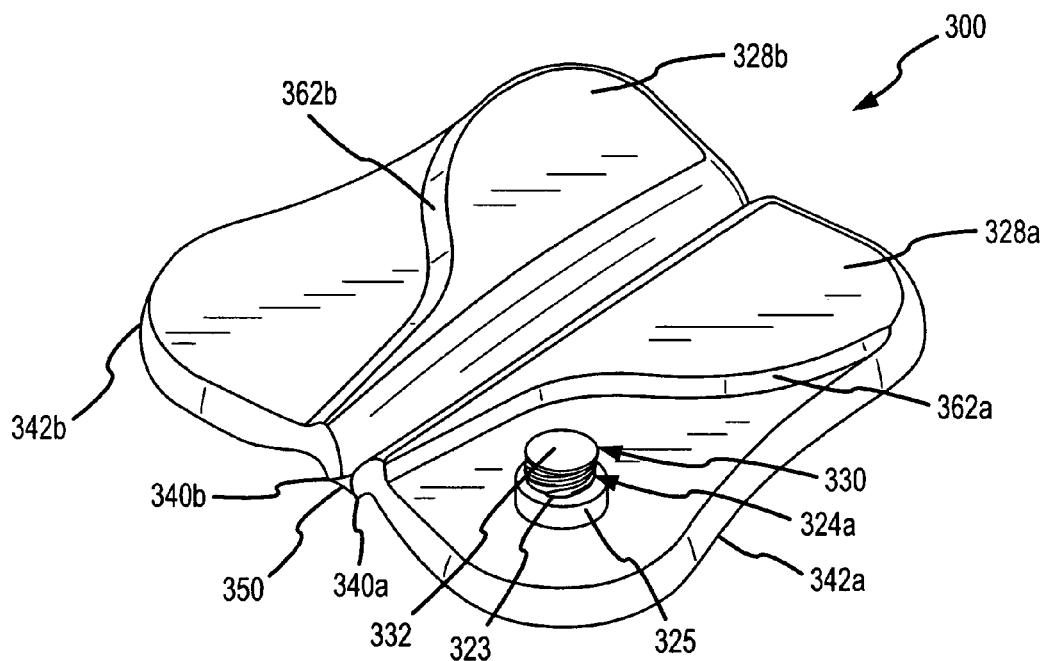

As previously indicated, the holding member 320 may include a tubular portion 324, wherein the opening 322 is located at a top end of the tubular portion 324. In this embodiment, and as best shown by FIGS. 10, 11A and 11B, the tubular portion 324 of the holding member may be defined by a first tubular section 324a and a second tubular section 324b. Further, the holding member 320 may comprise a first laterally-extending portion 328a interconnected to and extending away from the first tubular section 324a, and a second laterally-extending portion 328b interconnected to and extending away from the second tubular section 324b. Of note, the first and second laterally-extending portions 328a, 328b may have mirrored, outer configurations, wherein upon face-to-face adjoinment a smooth outer periphery is defined.

As shown in FIG. 10, at least the first tubular section 324a may include a plurality of longitudinal inner-sidewall grooves 370 so as to facilitate the depression and spring-back movement of the T-shaped member 330 during use. Optionally, an appropriate lubricant (e.g. a silicone-based lubricant) may be provided in grooves 370 prior to assembly/packaging/shipment to a user. Such lubricant may be provided by an outflow that occurs from and after molding of the T-shaped member 330 and insertion of the leg portion 336 thereof into the first tubular section 324a. Alternatively, or additionally, the lubricant may be separately applied to the grooves 370 or leg portion 336 of the T-shaped member 330 prior to insertion of the leg portion 336 of the T-shaped member 330 in first tubular section 324a.

Of further note, a base portion 364 may be provided at a bottom end of the tubular portion 324 for supportive or restraining engagement with a bottom end of the leg portion 336. Further, an upstanding post 366 may be provided on the base portion 364 to facilitate and maintain a centered position of the bottom end of leg portion 336 within the tubular portion 324.

With further reference to FIG. 10, it should be noted that the undulations on leg portion 336 of the T-shaped member may be sized differently in at least two sub-portions thereof. More particularly, in the illustrated embodiment the bottom three rings of undulations are of a first outside diameter that is less than an inside diameter of the second tubular section 324b yet greater than the inside diameter at the bottom end of the first tubular section 324a. Such an arrangement facilitates capture and retention of the leg portion 336 within the tubular portion 324. Of further note, the top three rings of undulations of the leg portion 336 have an outer diameter that is less than the inside diameter along the longitudinal extent of the first tubular section 324a, thereby facilitating depression and spring-back therethrough during use. As shown, the top ring of the undulations of leg portion 336 may be provided with a further-protruding center ring having an outer periphery that engages that inside sidewall of the tubular portion 324 (e.g. when the T-shaped member is in its initial configuration prior to docking and reassumes such configuration after docking).

As will be further described, the first laterally-extending portion 328a and second laterally-extending portion 328b may be interconnected along opposing first edges 340a, 340b by a hinge 350, wherein the docking apparatus 300 may be initially provided to a user with separated second edges 342a, 342b so as to define an open, clam-shell, or butterfly, configuration, as shown in FIGS. 11A and 11B (e.g. with pan-shaped, internal-facing sides shown in FIG. 11A and external-facing sides shown in FIG. 11B. The second edges 342a, 342b may be provided with one or more sets of complimentary connection members 352a, 352b, respectively, that allow for selective interconnection of the second side edges 342a and 342b when the docking apparatus 300 is closed. In this regard, when the docking apparatus 300 is closed, an end portion of the first tubular section 324a may be received, in a barrel fit manner, within an opposing portion of the second tubular section 324b. In another arrangement, one or more sets of complimentary connection members may be provided on the first tubular section 324a and second tubular section 324b, respectively, that allow for selective interconnection wherein the docking apparatus is closed.

In one approach, the connection members 352a, 352b may be provided for locking interconnection (e.g. restricting disconnection after a first connection therebetween). By way of example, and as shown in FIGS. 10 and 11A, the connection members 352b may comprise upstanding posts having enlarged tapered heads that define an undercut shelf. Correspondingly, the connection members 352a may comprise notches sized to receive the enlarged heads of the connection members 352b wherein tapered surfaces of the enlarged heads cam against rim portions of the notches during interconnection, and wherein the rim portions abuttingly engage the undercut shelves of the enlarged heads upon interconnection as to restrict disconnection.

In use, a user may initially position the docking apparatus 300 adjacent to a length of tubing at a patient care site, e.g. adjacent and parallel to hinge 350 so that the tubing will extend between the first and second laterally-extending portions 328a and 328b when closed. Then the opposing second side edges 350a and 350b of the first and/or second laterally-extending portions 328a and 328b may be pivotally advanced and interconnected by connection members 352a, 352b so as to retentively engage the docking apparatus 300 to the tubing length.

As illustrated in FIG. 11A, the first and second laterally-extending portions of 328a and 328b may further comprise offset internal walls 358a and 358b to enhance retentive engagement to a tubing length. That is, the offset walls 358a, 358b may be sized and positioned so that opposing edges of the walls 358a, 358b non-occlusively engage an interconnected tubing length at offset locations so as to cause the tubing length to follow an S-shaped, or tortuous, path through the docking apparatus 300. Such engagement may be provided to allow for slidable movement of the docking apparatus 300 along a tubing length by a user, yet provide for the maintenance of a given established position. To enhance structural integrity and the alignability of the connection member sets 352a, 352b during closure of the docking apparatus, slot members 356a, 356b may be provided on the first and second laterally-extending portions 328a, 328b, for receipt of corresponding end portions of offset walls 358b, 358a, respectively. Of further note, and as shown in FIGS. 9A, 9D and 9E, coincidental portions of the second side edges 342a, 342b adjacent to each end of the hinge 350 may be receded, or otherwise contoured to define apertures 368 for receipt and passage of a tubing length when the docking apparatus 300 is clamped in a closed position onto the tubing length.

Figure 12:
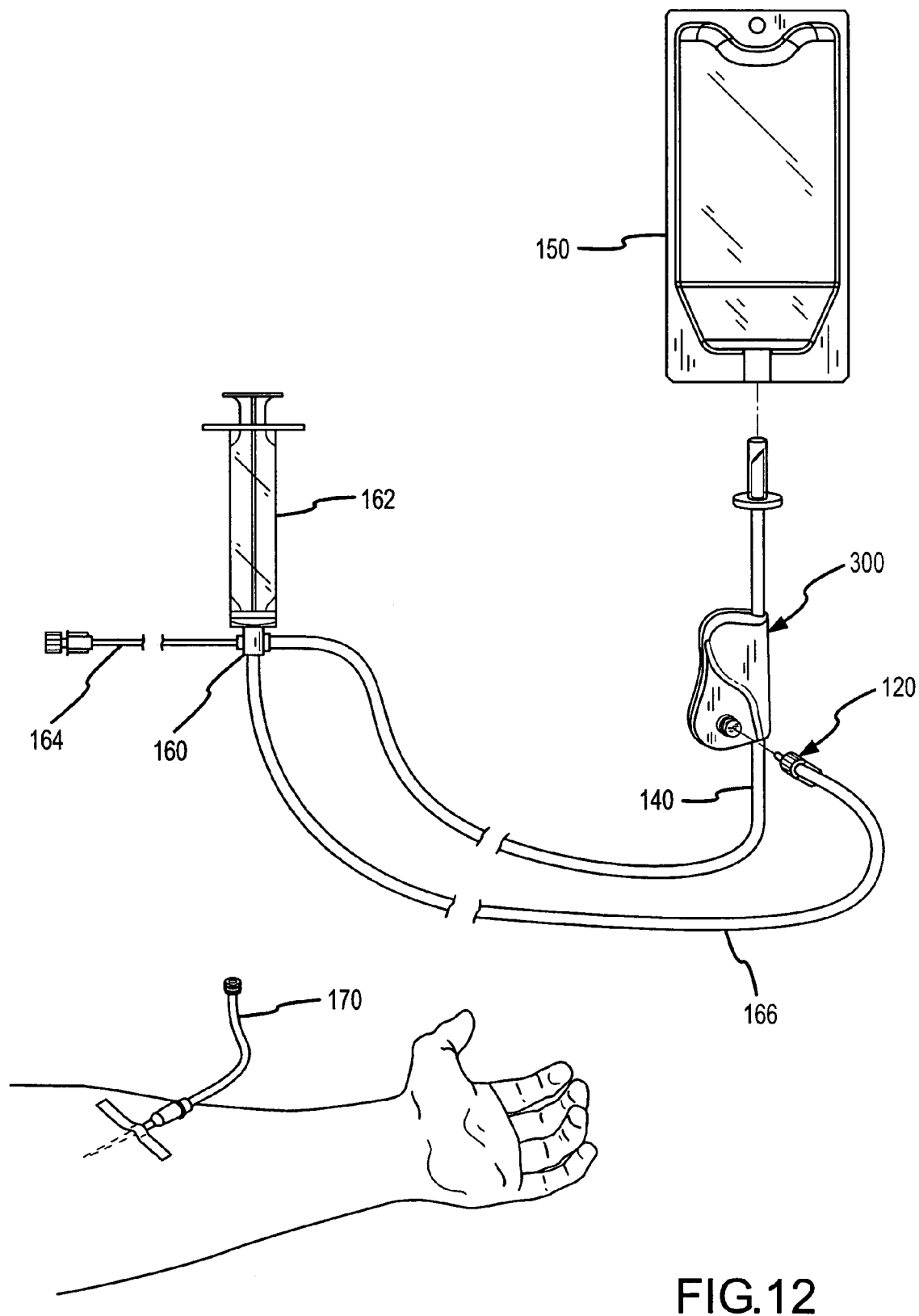
FIG. 12 illustrates the docking apparatus embodiment of FIGS. 9A-9G interconnected to a tubing length at a patient care site.

With reference now to FIG. 12, docking apparatus 300 is shown interconnected to a tubing length 140 comprising a tubing line set for vascular administration of a medical liquid. By way of example, a saline solution source 150 may be fluidly interconnected by tubing length 140 to a valve 160 fluidly interconnected to a syringe-like device 162. In turn, the valve 160 may also be fluidly interconnected to a tubing length 164 for selective interconnection to a liquid medication source. The valve 160 may also be fluidly interconnected to a tubing length 164 for selective interconnection to a vascular administration access device 170 via a male connector 120. As may be appreciated, the saline solution source 150 may comprise a bag that is supportable in an elevated position at a patient care site, wherein the interconnected docking apparatus 300 is readily accessible for docking the male connector 120 during periods of non-use.

Referring now and again to FIGS. 9A, 9F and 9G, it may be noted that the docking apparatus 300 is configured for handheld use. In particular, in a closed configuration the docking apparatus 300 is relatively compact (e.g. having a thickness of between about 0.375 in. and 0.875 in.) (e.g. about 0.5 in.), a length of between about 2.0 in. and 4.0 in. (e.g. about 3.0 in.) and a width of between about 1.0 in. and 2.0 in. (e.g. about 1.5 in.). Additionally, the docking apparatus may be of a relatively uniform thickness across the lateral extent thereof (e.g. varying by less than 20%), apart from the protruding first tubular section 324a. Further, the docking apparatus 300 includes opposing ends that are each at least partially rounded (e.g. at least about 90°) along, and otherwise second side edge portions 342a, 342b thereof, with a concave, or inwardly contoured, portion therebetween. As may be appreciated, the provision of opposing rounded end portions with a concave portion therebetween facilitates grasping by user. Additionally, by utilizing first and second laterally-extending portions 328a, 328b that are commonly configured in a mirror-like fashion, the realization of an ergonomic design is readily facilitated. Further, it may be noted that one of the rounded end portions of the first and second laterally-extending portions 328a, 328b is slightly larger than the other rounded end portion of the first and second laterally-extending portions 328a, 328b (e.g. a first rounded end portion has a greater radius of curvature than a second rounded end portion) so as to further facilitate grasping. In addition, the tubing portion 324 is coaxially located on a center axis of one of the rounded end portions to facilitate docking. Finally, it may be noted that in the illustrated embodiment the hinge 350 of docking apparatus 300 follows a substantially linear, or straight line path.

Figure 13:
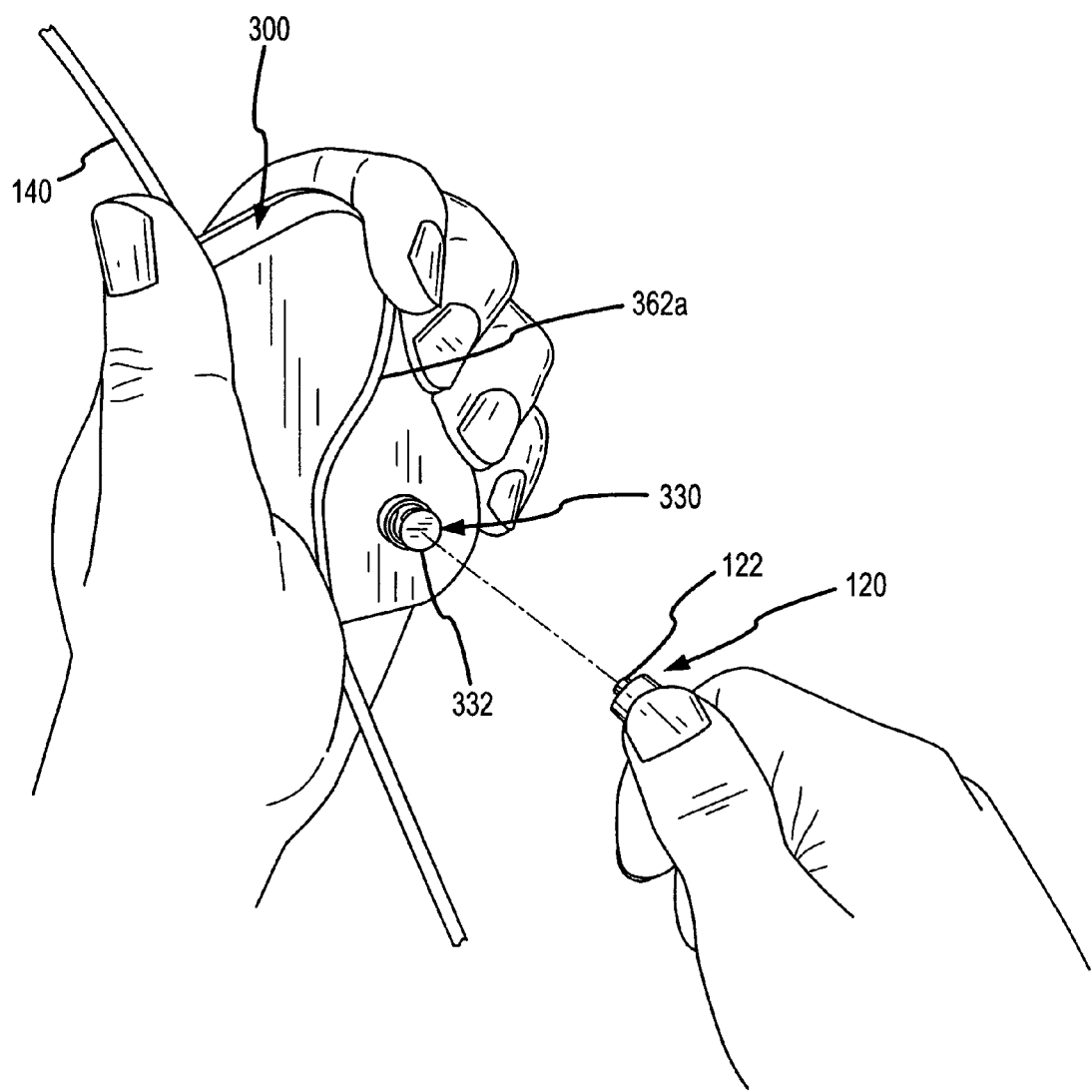
FIG. 13 is a perspective view of the docking apparatus embodiment of FIGS. 9A-9G interconnected to a tubing length portion and positioned by a user for docking receipt of a medical-liquid, male connector.

With reference now to FIG. 13, the docking apparatus 300 is illustrated interconnected to a tubing length 140 and grasped by the left hand of the user. Correspondingly, the user's right hand is holding the male connector 120 of the tubing length 140 illustrated in FIG. 12. As shown, the male connector 120 is in an aligned position relative to docking apparatus 300 for docking use. More particularly, the nozzle end 122 of the male connector 120 may be advanced towards the cap portion 332 so as to deform the T-shaped member 330 within the tubular portion 324 of the docking apparatus 300. Concomitantly, the collar 126 of the male connector 120 may be rotated clockwise relative to the docking apparatus 300 so as to restrainably interconnect the threaded interconnection surfaces 124 on collar 126 and 323 on tubular portion 324.

In relation to the illustrated docking apparatus 300, it should be noted that an external first purchase ledge 362a may be provided on the first laterally-extending portion 328a and may be engaged by a user's finger to facilitate stationary positioning of the docking apparatus 300 during rotative interconnection of a collar 126 of a male connector 120. In this regard, it should be noted that the first purchase ledge 362a extends at an angle across the outside face of the first laterally-extending portion 128a from the first side edge 340a thereof to the second side edge 342a thereof, thereby allowing the user to contact the purchase ledge 362a to provide an anchoring force to oppose the rotative force applied by the male connection collar 126 of the male connector 120 during interconnection.

Of additional note, while not shown, a protective cap may be located over the T-shaped member 330 as packaged and shipped for use. For example, a threaded cap may be interconnected to the thread interconnection surface 323 prior to initial use, and removed/discarded prior to a first docking procedure.

Figures 14A, 14B:
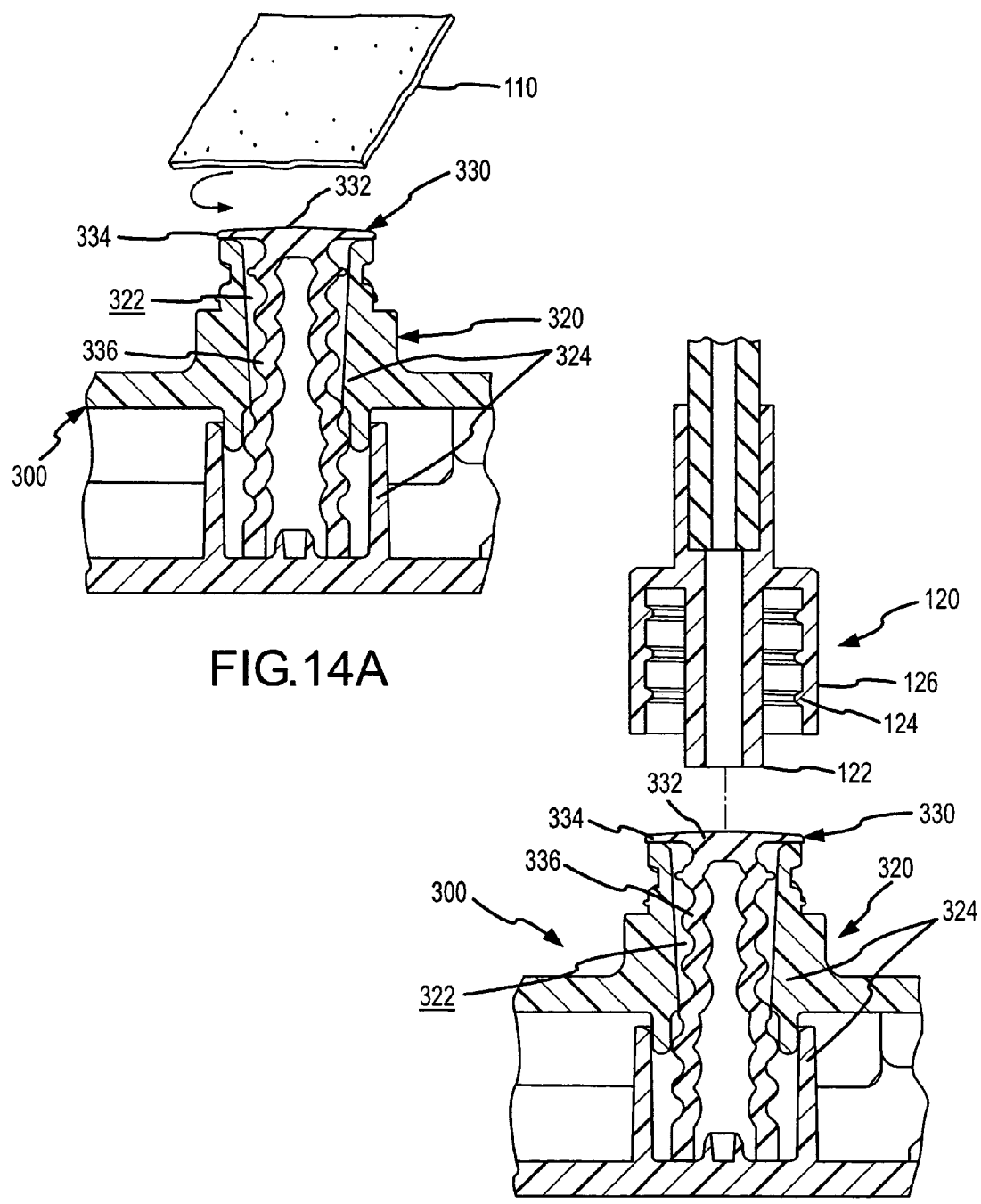
FIGS. 14A, 14B, 14C, 14D, 14E, 14F, 14G and 14H are side, cross-sectional views illustrating the use of the docking apparatus embodiment of FIGS. 9A-9G with a medical-liquid, male connector.

Reference is now made to FIGS. 14A-14F for further description of an exemplary use of the docking apparatus 300. As illustrated by FIG. 14A, prior to docking an antibacterial material may be applied to the top surface of the cap portion 332 using a swab 110. Then, as show in FIG. 14B, an exemplary medical-liquid, male connector 120 may be located in an aligned position with the opening 322 of docking apparatus 300. In this regard, a nozzle end 122 of the medical-liquid, male connector 120 may be visually aligned with a visibly distinct, top surface of the cap portion 332 of the T-shaped member 330. To initiate docking, the medical-liquid, male-connector 120 and/or docking apparatus 300 may be advanced so that the distal edge of the nozzle end 122 of medical-liquid, male-connector 120 engages the top surface portion of the cap portion 332 and the antibacterial material applied thereto.

Figure 14C:
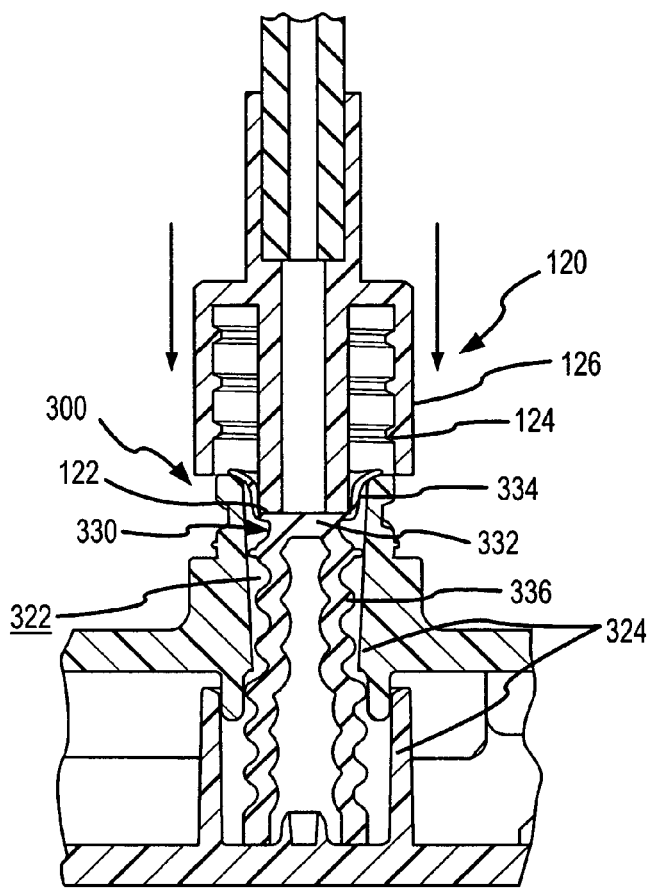

In FIG. 14C, as the nozzle end 122 of the medical-liquid, male-connector 120 has engaged and depressed the top surface of the cap portion to 332 of T-shaped member 330 into the top end of the tubular portion 324 of the holding member 320. More particularly, a portion of the flap region 334 has been drawn into the tubular portion 324, wherein the cap portion 332 has assumed a cup-shaped configuration. Concomitantly, the leg portion 336 of the T-shaped member 330 has been depressed within the tubular portion 324 of the docking apparatus 300.

Figure 14D:
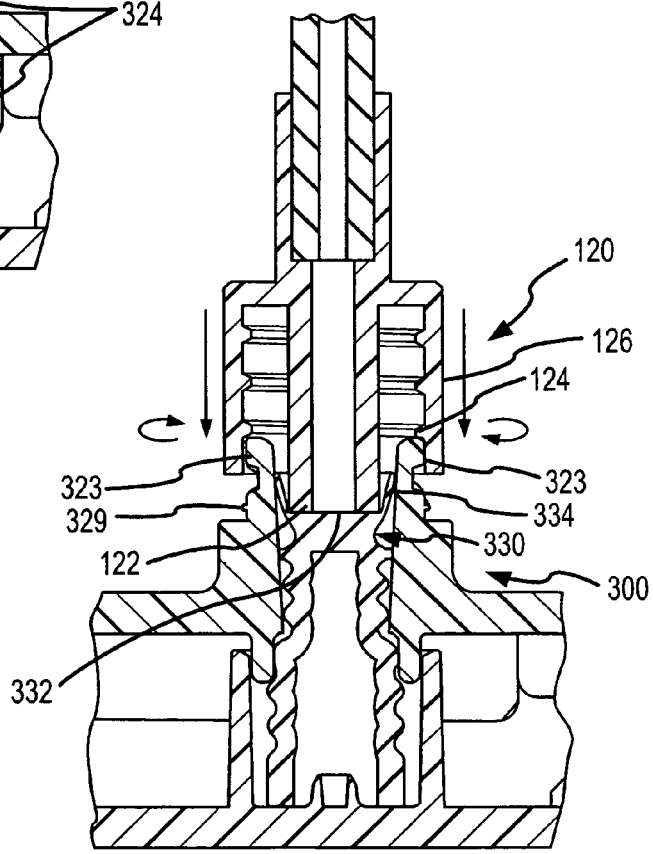

In FIG. 14D, the docking apparatus 300 and/or medical-liquid, male-connector 120 has been further advanced, wherein the cap portion 332 of the T-shaped member 330 has been further depressed into the tubular portion 324 of the holding member 320, thereby yielding a deeper cup-shaped configuration. Of note, the interconnection surface 124 on the inside surface of the collar 126 of the medical-liquid, male-connector 120 has interfaced with the threaded interconnection surface 323 provided on the tubular portion 324 of the holding member 320. As such, upon relative rotation the two interconnection surfaces will restrainably engage the medical-liquid, male-connector 120 and the docking apparatus 300 together.

Figure 14E:
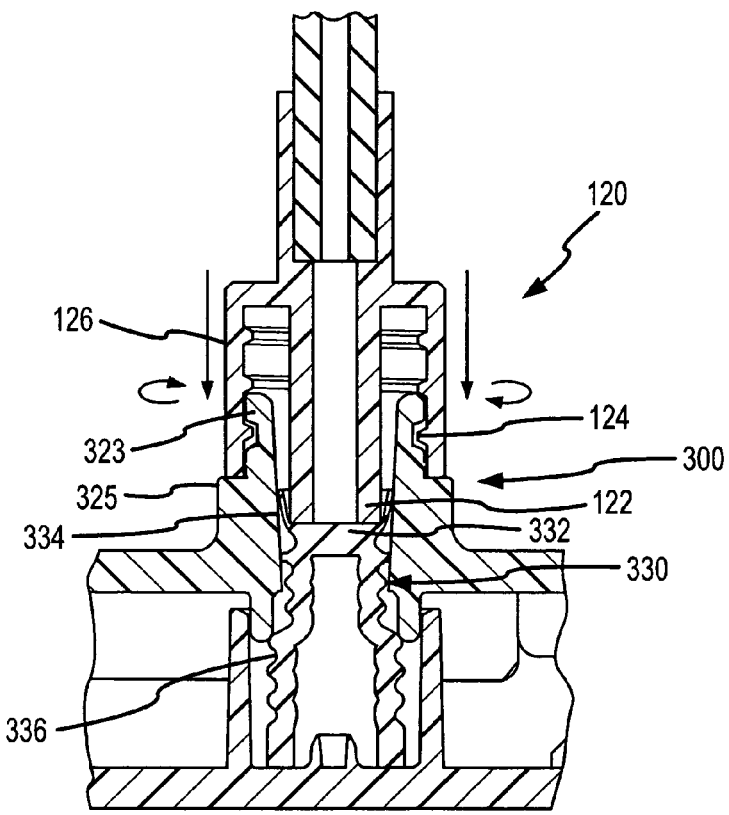

As shown in FIG. 14E, the collar 126 of the medical-liquid, male-connector 120 has been further rotated relative to the docking apparatus 300 to yield further threaded engagement. Concomitantly, the nozzle end 122 of the medical-liquid, male-connector 120 has been further advanced into the tube portion 360, thereby causing the cap portion 332 of the T-shaped member 330 to assume an even deeper cup-shaped configuration. As may be appreciated, such a cup-shaped configuration envelops the nozzle end 122 of the medical-liquid, male-connector 120 so as to facilitate the maintenance of the sterility thereof during docking. In this regard, it may also be noted that the initially exposed and treated surface (i.e. treated with an antibacterial material) of the flap region 334 of the cap portion 332 of the T-shaped member 330 is located between and adjacent to a distal sidewall portion of the nozzle end 122 of medical-liquid, male-connector 120 during docking, thereby further enhancing the maintenance of sterility.

As shown in FIG. 14E, the end of the collar 126 of medical-liquid, male connector had engaged the stop collar 325. In turn, further relative advancement is restricted, thereby indicating a desired docking interface to a user.

Figure 14F:
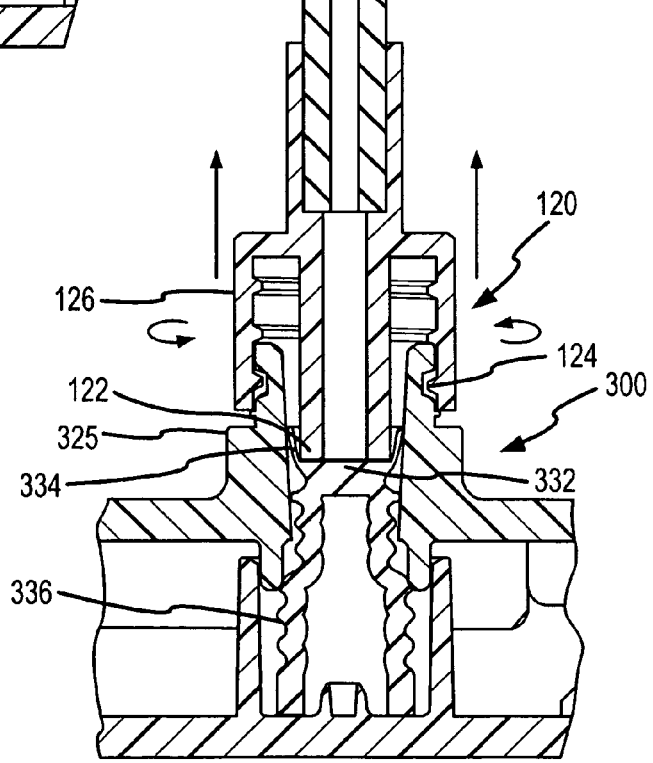
Figure 14G:
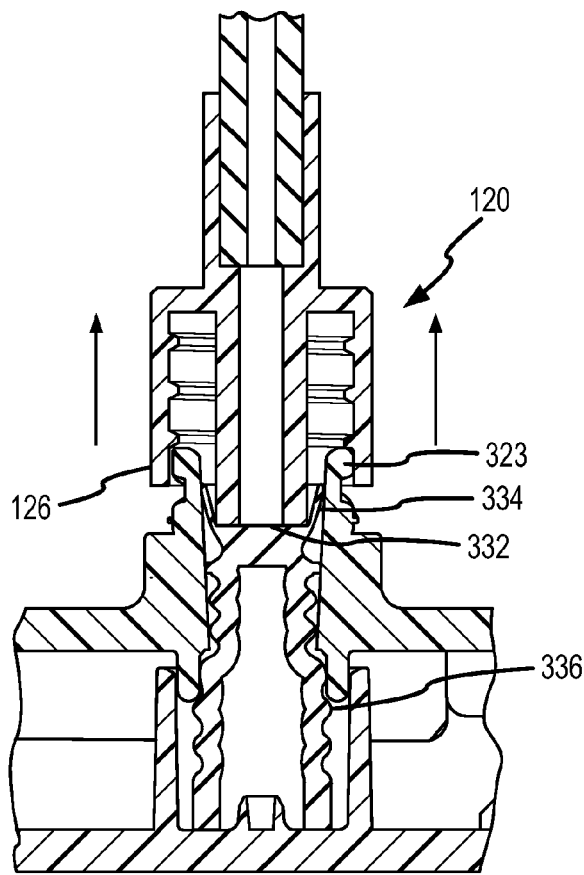
Figure 14H:
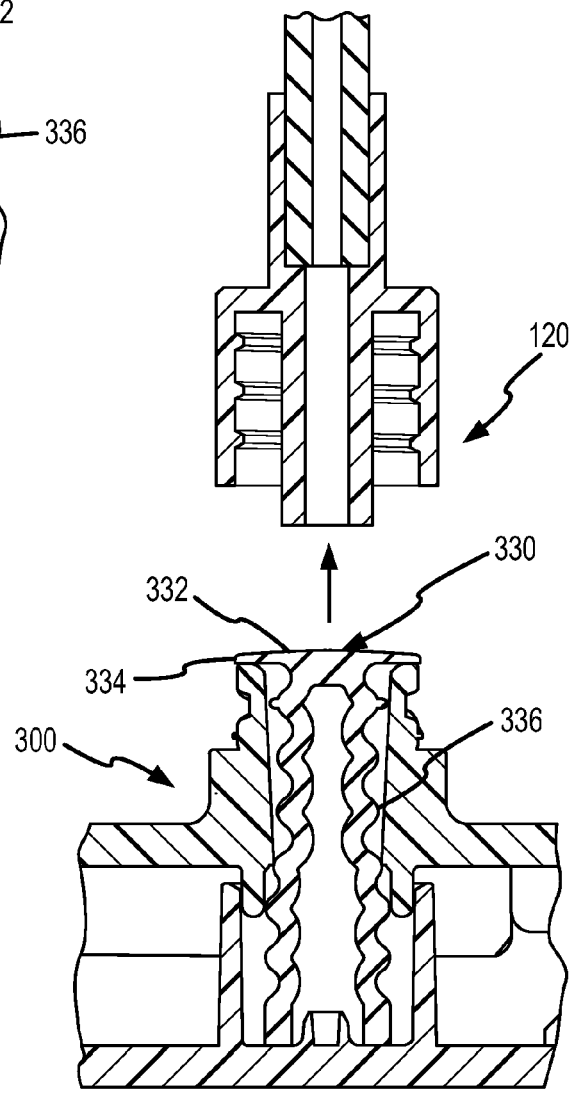

To terminate docking use, medical-liquid, male-connector 120 may be disconnected from the docking apparatus 300 by rotating the collar 126 as shown in FIGS. 14F and 14G, wherein the T-shaped member 330 will return to an initial configuration as shown in FIG. 14H. Of note, such configuration is the same configuration as shown in FIG. 14A. As may be appreciated, as the medical-liquid, male-connector 120 is rotatively retracted from the docking apparatus 300, the leg portion 336 of the T-shaped member 330 resiliently extends so as to urge the cap portion 332 back through the opening 322 so that the flap region 334 thereof again overlies the peripheral rim of the opening 322.

Figure 15:
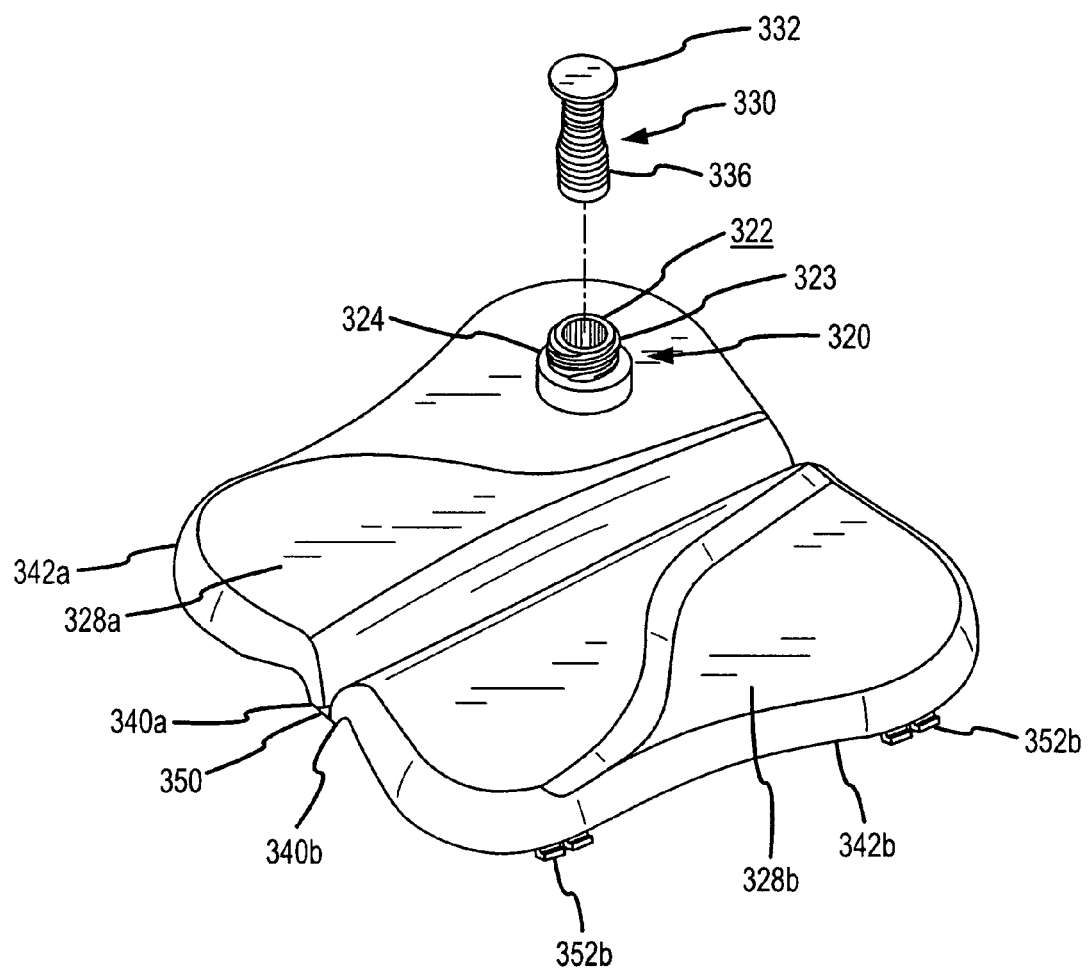
FIG. 15 is a perspective, assembly view of the docking apparatus embodiment of FIGS. 9A-9G in an open position.

Reference is now made to FIG. 15. As illustrated, the docking apparatus 300 may be constructed and assembled as a two-part operation. That is, the holding member 320 and any or all of the additional above-noted features of docking apparatus 300, other than those corresponding with the T-shaped member 330, may be integrally defined by a single molding production operation. For example, the first and second laterally-extending portions 328a, 328b and interconnected first and second tubular sections 324a, 324b, respectfully, the interconnecting hinge 350, and the various connection members and other features described above may be defined by a single, molded piece. Then, and as shown in FIG. 13, resilient, tubular leg portion 336 of the T-shaped member 330 may be simply, forcibly inserted through the top end of the opening 322 to yield the assembled docking apparatus 300 shown in FIGS. 11A and 11B. As previously noted, a lubricant may be applied to grooves 370 of the tubular portion 324 prior to insertion of the T-shaped member 330. After assembly, the docking apparatus 300 may be packaged. Prior to or after such packaging, the docking apparatus 300 may be sterilized. After packaging, the docking apparatus 300 may be shipped to a customer for use as otherwise described hereinabove.

The embodiments discussed above are not intended to limit the scope of the present invention and various modifications, adaptations, and extensions of the present invention will be apparent to those skilled in the art. Such further embodiments are all intended to be encompassed by the scope of the present invention as characterized by the claims that follow.

What is claimed is:

1. A medical-liquid, male connector docking apparatus, comprising:
   a holding member having a tubular portion for defining an opening for matably receiving a nozzle end of a medical-liquid, male connector therethrough; and,
   a T-shaped deformable member comprising:
   a cap portion extending over said opening in an initial configuration: and,
   a resilient leg portion adjoined to and extending away from said cap portion through said opening into said tubular portion when the cap portion is in said initial configuration;
   wherein said cap portion is deformable through said opening from said initial configuration over said opening to a cup-shaped configuration to envelop and thereby isolate a nozzle end of a medical-liquid, male connector insertable through said opening of the holding member.

2. A medical-liquid, male connector docking apparatus as recited in claim 1,
   wherein a portion of said cap portion of said deformable member is deformable for positioning over a nozzle end of a medical-liquid, male connector insertable through said opening of the holding member and between a portion of the tubular portion and a sidewall portion of a nozzle end of a medical-liquid, male connector insertable through said opening of the holding member.

3. A medical-liquid, male connector docking apparatus as recited in claim 1, wherein said cap portion of said T-shaped deformable member is reconfigured from said cup-shaped configuration to said initial configuration upon removal of a nozzle end of a medical-liquid, male connector from said opening of the holding member.

4. A medical-liquid, male connector docking apparatus as recited in claim 1, wherein said cap portion of said T-shaped member includes a pliable, peripheral, flap region, and wherein cap portion is deformable through said opening from said initial configuration to said cup-shaped configuration, and wherein said leg portion of said T-shaped member is depressible within said tubular portion by a nozzle end of a medical-liquid, male connector insertable through said opening of the holding member.

5. A medical-liquid, male connector docking apparatus as recited in claim 4, wherein said resilient, leg portion of said T-shaped member is operable to urge said cap portion of the T-shaped member through said opening for reconfiguration of said cap portion from said cup-shaped configuration to said initial configuration upon removal of a nozzle end of a medical-liquid, male connector from said opening of the holding member.

6. A medical-liquid, male connector docking apparatus as recited in claim 1, wherein said cap of said portion deformable member defines a continuous, outer surface portion across said opening prior to insertion of a nozzle end of a medical-liquid, male connector through said opening of the holding member.

7. A medical-liquid, male connector docking apparatus as recited in claim 6, wherein said cap of said portion deformable member extends over and laterally away from said opening prior to insertion of a nozzle end of a medical-liquid, male connector through said opening.

8. A medical-liquid, male connector docking apparatus as recited in claim 7, wherein said holding member includes:
   a tubular portion defining said opening.

9. A medical-liquid, male connector docking apparatus as recited in claim 8, wherein said tubular portion of said holding member comprises:
   an interconnection surface adapted for selective interconnection with a complimentary interconnection surface provided on a medical-liquid, male connector.

10. A medical-liquid, male connector docking apparatus as recited in claim 9, wherein said interconnection surface comprises:
    a threaded surface located on the outside of the tubular portion for receiving a complimentary threaded surface of a collar of a medical-liquid, male connector having a nozzle end insertable through said opening.

11. A medical-liquid, male connector docking apparatus as recited in claim 10, wherein said opening is located at a top end of said tubular portion.

12. A medical-liquid, male-connector docking apparatus as recited in claim 1, wherein said cap portion and said leg portion of said T-shaped member are integrally defined.

13. A medical-liquid, male-connector docking apparatus as recited in claim 12, wherein said T-shaped member comprises a polymer material.

14. A medical-liquid, male connector docking apparatus comprising:
    a holding member having an opening for matably receiving a nozzle end of a medical-liquid, male connector therethrough, wherein said holding member includes:
    a tubular portion defining said opening;
    a first laterally-extending portion interconnected to and extending laterally away from said tubular portion; and,
    a second laterally-extending portion hingedly interconnected to said first laterally-extending portion along at least a portion of opposing first side edges of said first and second laterally-extending portions to define a clam-shell configuration; and
    a deformable member disposed across said opening, wherein said deformable member is deformable through said opening to envelop and thereby isolate a nozzle end of a medical-liquid, male connector insertable through said opening of the holding member.

15. A medical-liquid, male connector docking apparatus as recited in claim 14, further comprising:
    connection members disposed on opposing second side edges of said first and second laterally-extending portions, said connection members being adapted for selective interconnection of said opposing second side edges of said first and second laterally-extending portions of said holding member.

16. A medical-liquid, male connector docking apparatus as recited in claim 15, wherein said connection members are adapted for one-way locking interconnection.

17. A medical-liquid, male connector docking apparatus as recited in claim 15, wherein said first laterally-extending portion is interconnected to and extends laterally away from a first section of said tubular portion, wherein said second-laterally-extending portion is interconnected to and extends laterally away from a second section of said tubular portion, and wherein upon interconnection of said second side edges of said first and second laterally-extending portions by said connection members said first and second sections of said tubular portion are coaxially aligned.

18. A medical-liquid, male connector docking apparatus as recited in claim 17 wherein said deformable member includes:
    a T-shaped member having a cap portion extending over said opening in an initial configuration; and,
    a leg portion adjoining and extending away from said cap member through said opening into said tubular portion when said cap portion is in said initial configuration, wherein said leg portion includes:
    a first leg portion located within said first section of said tubular portion when said cap portion is in said initial configuration, wherein said first leg portion has a maximum cross-dimension that is less than a minimum internal cross-dimension of said first section of the tubular portion; and,
    a second leg portion locatable within said second section of said tubular portion upon interconnection of said second side edges of said first and second laterally-extending portions by the connection members and, wherein said second leg portion has a maximum cross-dimension that is less than a minimum internal cross-dimension of said second section of the tubular portion and greater than said minimum internal cross-dimension of the first section of the tubular portion.

19. A medical-liquid, male connector docking apparatus as recited in claim 15, wherein said holding member is adapted so that a tubing length is positionable between said first and second laterally-extending portions and so that upon interconnection of said second side edges of said first and second laterally-extending portions by said connection members said docking apparatus is retentively engagable by said first and second laterally-extending portions to a tubing length.

20. A medical-liquid, male connector docking apparatus as recited in claim 19, wherein said holding member further includes:
    a first wall interconnected to and extending away from said first laterally-extending portion; and,
    a second wall interconnected to and extending away from said second laterally-extending portion, wherein said first wall and second wall are located in offset relation to define a tortuous path through said docking apparatus for a tubing length upon engagement thereto.

21. A medical-liquid, male connector docking apparatus as recited in claim 19, wherein the second side edges of each of said first laterally-extending portion and second laterally-extending portion include recessed portions, and wherein upon interconnection of said opposing second side edge portions said recessed portions of said first and second laterally-extending portions define apertures at opposing ends of said docking apparatus for passage of a tubing length therethrough.

22. A medical-liquid, male connector as recited in claim 15, wherein each of said first and second laterally-extending portions include:
    a first rounded end portion, wherein upon the connection of said connection members said tubular portion is coaxially positioned with said first rounded end portion of the first and second laterally-extending portions; and
    a second rounded end portion.

23. A medical-liquid, male connector as recited in claim 21, wherein each of said first and second laterally-extending portions further include:
    a concave side portion located between the first and second rounded end portions thereof.

24. A medical-liquid, male connector docking apparatus as recited in claim 1, wherein a portion of an outer surface of said deformable member is coaxially aligned with said opening and presented in a visually distinct manner.

25. A medical-liquid, male connector docking apparatus as recited in claim 24, wherein said portion of said outer surface of said film member corresponds in shape with said opening of said holding member.

26. A medical-liquid, male connector docking apparatus as recited in claim 1, wherein said deformable member comprises an antimicrobial material.

27. A medical-liquid, male connector docking apparatus as recited in claim 1, further comprising:
an interconnection surface adapted for selective interconnection with a complimentary interconnection surface provided on a medical-liquid, male connector, wherein said deformable member is disposed so that it is locatable in contact engagement with and between the interconnection surface and a complementary interconnection surface of a medical-liquid, male connector upon said selective interconnection.

28. A medical-liquid, male connector docking apparatus as recited in claim 27, wherein said deformable member extends across and laterally away from said opening.

29. A method for docking a medical-liquid, male connector, comprising:
engaging a nozzle end of a medical-liquid, male connector with an outer surface portion of a T-shaped deformable member, having a cap-portion in an initial configuration extending over and a leg portion extending through an opening of a holding member comprising a docking apparatus, by advancing at least one of said medical-liquid, male connector and said docking apparatus toward the other; and,
deforming said cap-portion of said deformable member of said docking apparatus from said initial configuration over said opening through said opening to a cup-shaped configuration to envelop said nozzle end of said medical-liquid, male connector by advancing at least one of said medical-liquid, male connector and said docking apparatus toward the other so that said nozzle end is inserted through said opening of the holding member of the docking apparatus.

30. A method as recited in claim 29, further comprising:
contacting said outer surface portion of said deformable member of the docking apparatus with an antibacterial material prior to said engaging and deforming steps.

31. A method as recited in claim 29, further comprising:
interconnecting said medical-liquid, male connector with said docking apparatus, wherein said nozzle end of the medical-liquid, male connector is maintained in said enveloped position.

32. A method as recited in claim 31, wherein a distal aspect of said nozzle end of the medical-liquid, male connector is maintained in contact engagement with said outer surface portion of the deformable member of the docking apparatus throughout said interconnecting step.

33. A method as recited in claim 31, said interconnecting step including:
interfacing an interconnection surface on said holding member of the docking apparatus in retentive relation with a complimentary interconnection surface of said medical-liquid, male connector.

34. A method as recited in claim 31, wherein said complimentary interconnection surface of said medical-liquid, male connector, is provided on a rotatable collar of the medical-liquid, male connector, and wherein said interconnecting step includes:
rotatably advancing said collar of the medical-liquid, male connector relative to said holding member of the docking apparatus.

35. A method as recited in claim 29, wherein said holding member includes a tubular portion defining said opening, and wherein said step of deforming said cap-portion of said deformable member includes:
positioning a portion of said deformable member over said nozzle end of the medical-liquid, male connector and between a portion of said tubular portion and a sidewall portion of the nozzle end of the medical-liquid, male connector.

36. A method as recited in claim 29, wherein said step of deforming said cap-portion of said deformable member includes:
depressing said leg portion of said T-shaped member.

37. A method as recited in claim 36, wherein said cap portion includes a peripheral flap region extending laterally away from said opening prior to said deforming step, and wherein said step of depressing said leg portion of said T-shaped member includes:
drawing said flap region through said opening wherein said cap portion defines said cup-shaped configuration.

38. A method as recited in claim 37, further comprising:
removing said nozzle end of the medical-liquid, male connector from the opening of the holding member; and,
utilizing a spring force of said leg portion to urge said cap portion through said opening to reconfigure said cap portion from said cup-shaped configuration to said initial configuration.

39. A method as recited in claim 29, further comprising:
interconnecting said docking apparatus to a tubing length at a patient care site.

40. A method as recited in claim 39, wherein said holding member of said docking apparatus includes a first laterally-extending portion and a second laterally-extending portion, and wherein said interconnecting step includes:
positioning the tubing length between said first laterally-extending portion and said second laterally-extending portion; and,
retentively engaging said tubing length between said first laterally-extending portion and said second laterally-extending portion.

41. A method as recited in claim 40, wherein said first and second laterally-extending portions are hingedly interconnected along opposing first side edges thereof and include connection numbers on second side edge portions thereof, and wherein said engaging step includes:
pivoting at least one of said second side edge portions of said first and second laterally-extending portions relative to the other so as to interconnect said connection members.

42. A method as recited in claim 41, wherein said interconnecting step further includes:
locking said first laterally-extending portion and second laterally-extending portion in an interconnected relationship to restrict removal of said docking apparatus from said tubing length.

43. A method as recited in claim 29, further comprising:
disconnecting said medical-liquid, male connector from said docking apparatus; and,
disengaging said nozzle end of the medical-liquid, male connector from said surface of the film member of the docking apparatus, wherein said surface of said deformable member returns to an initial position.

44. A method as recited in claim 43, further comprising:
repeating said engaging, stretching, interconnecting, disconnecting, and disengaging steps in plurality of times.

45. A method as recited in claim 29, further comprising:

providing a portion of said outer surface of said deformable member in coaxial alignment with said opening of the holding member, wherein said portion is presented in a visually distinct manner.

46. A method as recited in claim 45, wherein said visually distinct portion of said outer surface of the deformable member corresponds in shape with said opening of the holding member comprising the docking apparatus.

\* \* \* \* \*